(12) United States Patent
Helleday

(10) Patent No.: US 8,859,562 B2
(45) Date of Patent: Oct. 14, 2014

(54) USE OF RNAI INHIBITING PARP ACTIVITY FOR THE MANUFACTURE OF A MEDICAMENT FOR THE TREATMENT OF CANCER

(75) Inventor: Thomas Helleday, Stockholm (SE)

(73) Assignee: The University of Sheffield, Sheffield (GB)

( * ) Notice: Subject to any disclaimer, the term of this patent is extended or adjusted under 35 U.S.C. 154(b) by 2568 days.

(21) Appl. No.: 10/555,507

(22) PCT Filed: Jul. 23, 2004

(86) PCT No.: PCT/GB2004/003235
§ 371 (c)(1),
(2), (4) Date: Sep. 15, 2006

(87) PCT Pub. No.: WO2005/012524
PCT Pub. Date: Feb. 10, 2005

(65) Prior Publication Data
US 2007/0179160 A1    Aug. 2, 2007

(30) Foreign Application Priority Data

Jul. 25, 2003   (GB) .................................. 0317466.1

(51) Int. Cl.
| | | |
|---|---|---|
| A61K 31/495 | (2006.01) | |
| A61K 31/33 | (2006.01) | |
| A61K 31/435 | (2006.01) | |
| A61K 38/00 | (2006.01) | |
| C07D 487/06 | (2006.01) | |
| C12N 15/113 | (2010.01) | |
| A61K 31/5517 | (2006.01) | |

(52) U.S. Cl.
CPC ............ *C07D 487/06* (2013.01); *A61K 38/005* (2013.01); *C12N 15/1137* (2013.01); *A61K 31/5517* (2013.01); *C12Y 204/0203* (2013.01); *C12N 2310/14* (2013.01)
USPC .......................... 514/258.1; 514/299; 514/388

(58) Field of Classification Search
None
See application file for complete search history.

(56) References Cited

U.S. PATENT DOCUMENTS

| | | | |
|---|---|---|---|
| 5,098,861 A | 3/1992 | Blackstone | |
| 5,484,951 A | 1/1996 | Kun et al. | |
| 5,519,053 A | 5/1996 | Kun et al. | |
| 5,652,367 A | 7/1997 | Kun et al. | |
| 6,548,494 B1 * | 4/2003 | Webber et al. ................ | 514/220 |
| 7,072,771 B2 * | 7/2006 | Oliveira .......................... | 702/27 |
| 7,087,637 B2 | 8/2006 | Grandel et al. | |
| 7,176,188 B2 | 2/2007 | Desnoyers | |
| 2003/0229004 A1 | 12/2003 | Zarling et al. | |
| 2005/0227919 A1 | 10/2005 | Ashworth et al. | |
| 2006/0142231 A1 | 6/2006 | Ashworth et al. | |

FOREIGN PATENT DOCUMENTS

| | | |
|---|---|---|
| EP | 0600831 A1 | 11/1993 |
| WO | WO 95/24379 | 9/1995 |
| WO | WO 9908680 A1 * | 2/1999 |
| WO | 00/42040 | 7/2000 |
| WO | 01/16136 | 3/2001 |
| WO | WO 02/12239 | 2/2002 |
| WO | WO 02/36576 A1 | 5/2002 |
| WO | WO 02/090334 A1 | 11/2002 |
| WO | WO 03/014090 A1 | 2/2003 |
| WO | WO 03/063874 A1 | 8/2003 |
| WO | WO 03/070234 A1 | 8/2003 |
| WO | WO 03/093261 A1 | 11/2003 |
| WO | WO 2004/008976 A1 | 1/2004 |

OTHER PUBLICATIONS

Gan et al., Specific interference with gene expression and gene function mediated by long dsRNA in neural cells, Journal of Neuroscience Methods, 121, 2002, pp. 151-157.*

Cecil Textbook of Medicine, 1997, 20th Edition, vol. 1, pp. 1007-1010.*

Sausville et al. (Cancer Research, 2006, vol. 66, pp. 3351-3354).*

Johnson et al. (British J. of Cancer, 2001, 84(10):1424-1431).*

Thacker, J., Cancer Letters, 2005, vol. 219, pp. 125-135.*

BG483078, http://mgc.nci.nih.gov/, National Institutes of Health, Mammalian Gene Collection (MGC, Unpublished, 1999, Contact: Robert Strausberg, Ph.D, Tissue Procurement: CLONTECH Laboratories, Inc.

Elbashir et al., Duplexes of 21-Nucleotide RNAs Mediate RNA Interference in Cultured Mammalian Cells, Nature, 2001, 411: 494-498.

Larminat et al., Deficiency in BRCA2 Leads to Increase in Nonconservative Homologous Recombination, Oncogene, 2002, 21: 5188-5192.

Massuda et al., PARP Inhibitor, Down-Regulates Metastasis Associated S100A4 (MTS1) and Suppresses Invasion of Breast Cancer Cells In Vitro, Proceedings of the American Association for Cancer Research, 2003, 44($2^{nd}$ ed), 867-868.

Schultz et al., Poly (ADP-Ribose) Polymerase (PARP-1) Has a Controlling Role in Homologous Recombination, Nucleic Acids Research, 2003, 31(17): 4959-4964.

Shall et al., Poly(DP-Ribose) Polymerase-1: What Have We Learned From the Deficient Mouse Model?, Mutation Research, 2000, 460: 1-15.

Weltin et al., Effect of 6(5H)-Phenanthridinone, An Inhibitor of Poly(ADP-Ribose) Polymerase, on Cultured Tumor Cells, Oncology Research, 6(9): 399-403.

(Continued)

*Primary Examiner* — James D Anderson
(74) *Attorney, Agent, or Firm* — Bozicevic, Field & Francis LLP; Pamela J. Sherwood

(57) ABSTRACT

The present invention relates to the use of an agent that inhibits the activity of an enzyme that mediates repair of a DNA strand break in the manufacture of a medicament for the treatment of diseases caused by a defect in a gene that mediates homologous recombination.

1 Claim, 20 Drawing Sheets

(56) References Cited

OTHER PUBLICATIONS

Gallmeier et al., Absence of Specific Cell Killing of the BRCA2-Deficient Human Cancer Cell Line CAPAN1 by Poly(ADP-Ribose) Polymerase Inhibition, 2005 Cancer Biol. & Ther., 4(7): 703-706.
McCabe et al., BRCA2-Deficient CAPAN-1 Cells Are Extremely Sensitive to the Inhibition of Poly (ADP-Ribose) Polymerase, 2005, Cancer Biol. & Ther., 4(9): 934-936.
Jönsson, Göran; et al., "High-Resolution Genomic Profiles of Breast Cancer Cell Lines Assessed by Tiling BAC Array Comparative Genomic Hybridization", Genes, Chromosomes and Cancer, 2007, 46:543-558.
Sanger Institute database entry for MDA_MB-231, Catalogue of Somatic Mutations in Cancer, 2 pgs.
Turner, Nicholas; et al., "Hallmarks of 'BRCAness' in sporadic cancers", Nature Reviews, Oct. 2004, 4:1-6.
Wooster, Richard; et al., "Breast and Ovarian Cancer", The New England Journal of Medicine, Jun. 5, 2003, 348:2339-47.
Bernstein, C., et al., "DNA repair/pro-apoptotic dual-role proteins in five major DNA repair pathways: fail-safe protection against carcinogenesis," (2002) *Mutation Research*, 511:147-178.
Bryant, H., et al., "Specific killing of BRCA2-deficient tumours with inhibitors of poly(ADP-ribose) polymerase," (2005) *Nature*, 434:913-917.
Farmer, H., et al., "Targeting the DNA repair defect in *BRCA* mutant cells as a therapeutic strategy," (2005) *Nature*, 434:917-921.
Watchers, F., et al., "Selective targeting of homologous DNA recombination repair by gemcitabine," (2003) *Int. J. Radiation Oncology Biol. Phys.*, 57(2):553-562.
Banasik, Marek; et al., "Specific Inhibitors of Poly (ADP-Ribose) Synthetase and Mono (ADP-Ribosyl) transferase", The Journal of Biological Chemistry, Jan. 25, 1992, 267(3):1569-1575.
Calabrese, Christopher R; et al., "Identification of Potent Nontoxic Poly (ADP-Ribose) Polymerase-1 Inhibitors: Chemopotentiation and Pharmacological Studies", Clinical Cancer Research, Jul. 2003, 9:2711-2718.
Cepeda, Victoria; et al., "Poly (ADP-Ribose) Polymerase-1 (PARP-1) Inhibitors in Cancer Chemotherapy", Recent Patents on Anti-Cancer Drug Discovery, 2006, 1:39-53.
Dillon, Krystyna J; et al., "A FlashPlate Assay for the Identification of PARP-1 Inhibitors", J. Biomol Screen, 2003, 8(3):347-352.
Ferraris, Dana; et al., "Design and Synthesis of Poly ADP-ribose Polymerase-1 Inhibitors. 2. Biological Evaluation of Aza-5[H]-phenanthridin-6-ones as Potent, Aqueous-Soluble Compounds for the Treatment of Ischemic Injuries", J. Med. Chem., 2003, 46:3138-3151.
Griffin, RJ; et al., "The role of inhibitors of poly (ADP-ribose) polymerase as resistance-modifying agents in cancer therapy", Biochimie, 1995, 77:408-422.
McCabe, Nuala; et al., "Deficiency in the Repair of DNA Damage by Homologous Recombination and Sensitivity to Poly (ADP-Ribose) Polymerase Inhibition", Cancer Res, Aug. 15, 2006, 66(16):8109-8115.
Virag, Laszlo; et al., "The Therapeutic Potential of Poly (ADP-Ribose) Polymerase Inhibitors", Pharmacological Reviews, 2002: 54(3):375-429.
Dudas, Andrej; et al., "DNA double-strand break repair by homologous recombination", Mutation Research, 2004, 566:131-167.
Hoeijmakers, Jan H. J.; et al., "Genome maintenance mechanisms for preventing cancer", Nature, May 17, 2001, 411:366-374.
Khanna, Kum Kum; et al., "DNA double-strand breaks: signaling, repair and the cancer connection", Nature Genetics, Mar. 2001, 27:247-254.
Fong; et al., "AZD2281 (KU-0059436), a PARP (poly ADP-ribose polymerase) inhibitor with single agent anticancer activity in patients with BRCA deficient ovarian cancer: Results from a phase I study", J Clin Oncol 26: 2008 (May 20 suppl; abstr 5510).
Hao; et al., "BRCA1-IRIS activates cyclin D1 expression in breast cancer cells by downregulating the JNK phosphatase DUSP3/VHR", Int. J. Cancer (2007), 121:39-46.
Lau; et al., "Pre-clinical activity of the PARP inhibitor AZD2281 in homologous recombination repair deficient triple negative breast cancer", EORTIC 2008 Geneva, poster #557.
Calabrese; et al., "Identification of Potent Nontoxic Poly(ADP-Ribose) Polymerase-1 Inhibitors: Chempotentiation and Pharmacological Studies", Clinical Cancer Research (2003), 9:2711-2718.
Berthet; et al., "DNA repair inhibitors", Expert Opinion on Therapeutic Patents (1999), 9(4):401-415.
Perkins, et al., "Novel Inhibitors of Poly(ADP-ribose) Polymerase/PARP1 and PARP2 Identified Using a Cell-based Screen in Yeast", Cancer Research (2001), 61:4175-4183.

\* cited by examiner

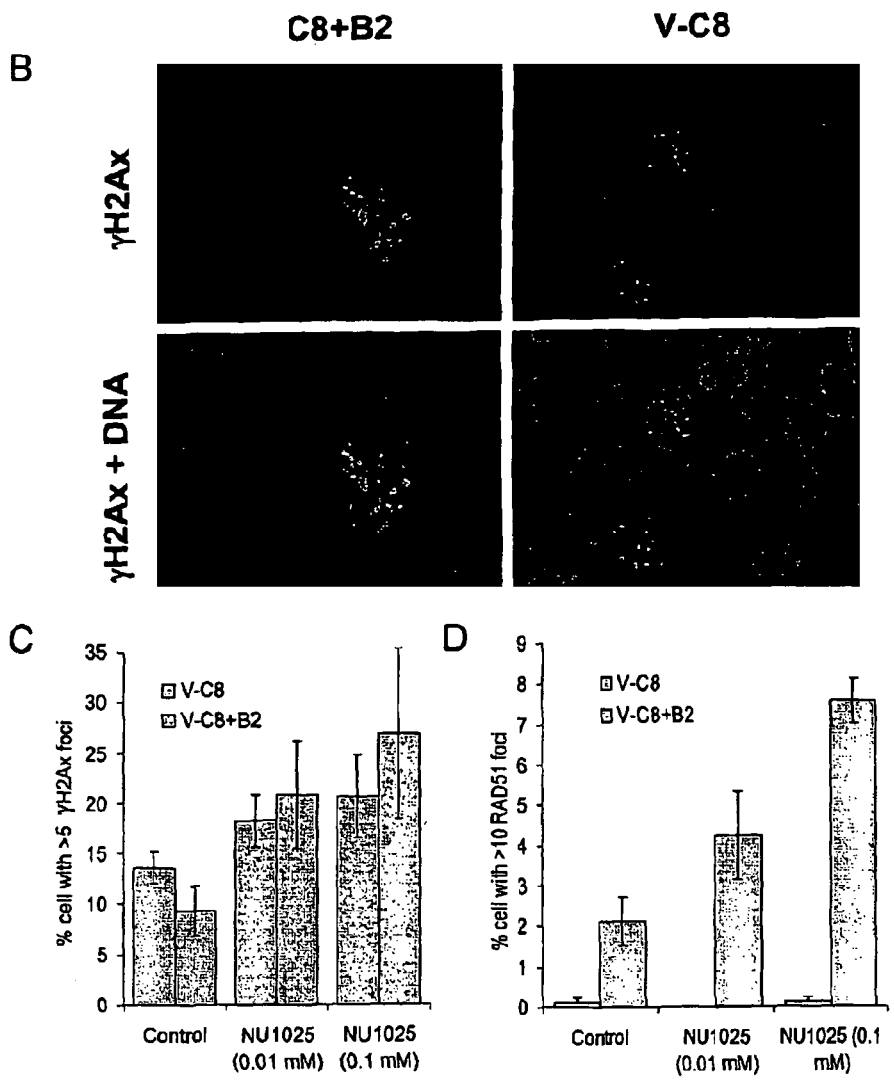
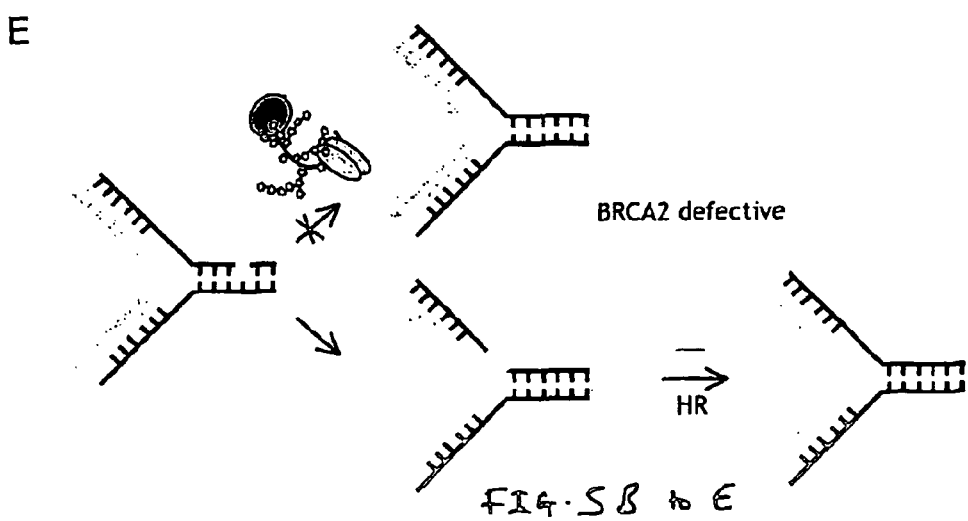
FIG. 5B to E

FIGURE 9

```
   1 cgcccgccca gccccggggg cagggaaagc ctaaattacg gaattaccgc gagcaaggag
  61 cgcggaatcg gggagcgtcc ggagctagct ggatcctcta ggcaggatgg tgatgggaat
 121 ctttgcaaat tgtatcttct gtttgaaagt gaagtactta cctcagcagc agaagaaaaa
 181 gctacaaact gacattaagg aaaatggcgg aaagttttcc ttttcgttaa atcctcagtg
 241 cacacatata atcttagata atgctgatgt tctgagtcag taccaactga attctatcca
 301 aaagaaccac gttcatattg caaacccaga ttttatatgg aaatctatca gagaaaagag
 361 actcttggat gtaaagaatt atgatcctta taagcccctg gacatcacac cacctcctga
 421 tcagaaggcg agcagttctg aagtgaaaac agaaggtcta tgcccggaca gtgccacaga
 481 ggaggaagac actgtggaac tcactgagtt tggtatgcag aatgttgaaa ttcctcatct
 541 tcctcaagat tttgaagttg caaaatataa caccttggag aaagtgggaa tggagggagg
 601 ccaggaagct gtggtggtgg agcttcagtg ttcgcgggac tccagggact gtcctttcct
 661 gatatcctca cacttcctcc tggatgatgg catggagact agaagacagt ttgctataaa
 721 gaaaacctct gaagatgcaa gtgaatactt tgaaaattac attgaagaac tgaagaaaca
 781 aggatttcta ctaagagaac atttcacacc tgaagcaacc caattagcat ctgaacaatt
 841 gcaagcattg cttttggagg aagtcatgaa ttcaagcact ctgagccaag aggtgagcga
 901 tttagtagag atgatttggg cagaggccct gggccacctg gaacacatgc ttctcaagcc
 961 agtgaacagg attagcctca acgatgtgag caaggcagag gggattctcc ttctagtaaa
1021 ggcagcactg aaaaatggag aaacagcaga gcaattgcaa aagatgatga cagagtttta
1081 cagactgata cctcacaaag gcacaatgcc caaagaagtg aacctgggac tattggctaa
1141 gaaagcagac ctctgccagc taataagaga catggttaat gtctgtgaaa ctaatttgtc
1201 caaacccaac ccaccatccc tggccaaata ccgagctttg aggtgcaaaa ttgagcatgt
1261 tgaacagaat actgaagaat ttctcagggt tagaaaagag gttttgcaga atcatcacag
1321 taagagccca gtggatgtct tgcagatatt tagagttggc agagtgaatg aaaccacaga
1381 gtttttgagc aaacttggta atgtgaggcc cttgttgcat ggttctcctg tacaaaacat
1441 cgtgggaatc ttgtgtcgag ggttgctttt acccaaagta gtggaagatc gtggtgtgca
1501 aagaacagac gtcggaaacc ttggaagtgg gatttatttc agtgattcgc tcagtacaag
1561 tatcaagtac tcacacccgg gagagacaga tggcaccaga ctcctgctca tttgtgacgt
1621 agccctcgga aagtgtatgg acttacatga gaaggacttt tccttaactg aagcaccacc
1681 aggctacgac agtgtgcatg gagtttcaca aacagcctct gtcaccacag actttgagga
1741 tgatgaattt gttgtctata aaaccaatca ggttaaaatg aaatatatta ttaaattttc
1801 catgcctgga gatcagataa aggactttca tcctagtgat catactgaat tagaggaata
1861 cagacctgag ttttcaaaatt ttttcaaaggt tgaagattac cagttaccag atgccaaaac
1921 ttccagcagc accaaggccg gcctccagga tgcttctggg aacttggttc ctctggagga
1981 tgtccacatc aaagggagaa tcatagacac tgtagcccag gtcattgttt ttcagacata
2041 cacaaataaa agtcacgtgc ccattgaggc aaaatatatc tttcctttgg atgacaaggc
2101 cgctgtgtgt ggcttcgaag cctttcatcaa tgggaagcac atagttggag agattaaaga
2161 gaaggaagaa gcccagcaag agtacctaga agccgtgacc cagggccatg gcgcttacct
2221 gatgagtcag gatgctccgg acgttttttac tgtaagtgtt ggaaacttac ccctaaggc
2281 taaggttctt ataaaaatta cctacatcac agaactcagc atcctgggca ctgttggtgt
2341 ctttttcatg cccgccaccg tagcaccctg gcaacaggac aaggctttga atgaaaacct
2401 tcaggataca gtagagaaga tttgtataaa agaaatagga acaaagcaaa gcttctcttt
2461 gactatgtct attgagatgc cgtacgtgat tgaattcatt ttcagtgata ctcatgaact
2521 gaaacaaaag cgcacagact gcaaagctgt cattagcacc atggaaggca gctccttaga
2581 cagcagtgga ttttctctcc acatcggttt gtctgctgcc tatctcccaa gaatgtgggt
2641 tgaaaaacat ccagaaaaag aaagcgaggc ttgcatgctt gtcttcaac ccgatctcga
2701 tgtcgacctc cctgacctag ccaatgagag cgaagtgatt atttgtcttg actgctccag
2761 ttccatggag ggtgtgacat tcttgcaagc caaggaaatc gccttgcatg cgctgtcctt
```

```
2821 ggtgggtgag aagcagaaag taaatattat ccagttcggc acaggttaca aggagctatt
2881 ttcgtatcct aagcatatca caagcaatac cgcggcagca gagttcatca tgtctgccac
2941 acctaccatg gggaacacag acttctggaa aacactccga tatcttagct tattgtaccc
3001 tgctcgaggg tcacggaaca tcctcctggt gtctgatggg cacctccagg atgagagcct
3061 gacattacag ctcgtgaaga ggagccgccc gcacaccagg ttattcgcct gcggtatcgg
3121 ttctacagca aatcgtcacg tcttaaggat tttgtcccag tgtggtgccg gagtatttga
3181 atatttaat gcaaaatcca agcatagttg gagaaaacag atagaagacc aaatgaccag
3241 gctatgttct ccgagttgcc actctgtctc cgtcaaatgg cagcaactca atccagatgc
3301 gcccgaggcc ctgcaggccc cagcccaggt gccatccttg tttcgcaatg atcgactcct
3361 tgtctatgga ttcattcctc actgcacaca ggcaactctg tgtgcactaa ttcaagagaa
3421 agaattttgt acaatggtgt cgactactga gcttcagaag acaactggaa ctatgatcca
3481 caagctggca gcccgagctc taatcagaga ttatgaagat ggcattcttc acgaaaatga
3541 aaccagtcat gagatgaaaa aacaaacctt gaaatctctg attattaaac tcagtaaaga
3601 aaactctctc ataacacaat ttacaagctt tgtggcagtt gagaaaaggg atgagaatga
3661 gtcacctttt cctgatattc caaaagtttc tgaacttatt gccaaagaag atgtagactt
3721 cctgccctac atgagctggc aggggggaacc ccaagaagcc gtcaggaacc agtctctttt
3781 agcatcctct gagtggccag aattacgttt atccaaacga aaacatagga aaattccatt
3841 ttccaaaaga aaatggaat tatctcagcc agaagtttct gaagattttg aagaggatgc
3901 cttaggtgta ctaccagctt tcacatcaaa tttggaacgt ggacgtgtgg aaaagctatt
3961 ggatttaagt tggacagagt catgtaaacc aacagcaact gaaccactat ttaagaaagt
4021 cagtccatgg gaaacatcta cttctagctt ttttcctatt ttggctccgg ccgttggttc
4081 ctatcttacc ccgactaccc gcgctcacag tcctgcttcc ttgtcttttg cctcatatcg
4141 tcaggtagct agtttcggtt cagctgctcc tcccagacag tttgatgcat ctcaattcag
4201 ccaaggccct gtgcctggca cttgtgctga ctggatccca cagtcggcgt cttgtcccac
4261 aggacctccc cagaacccac cttctgcacc ctattgtggc attgtttttt cagggagctc
4321 attaagctct gcacagtctg ctccactgca acatcctgga ggctttacta ccaggccttc
4381 tgctggcacc ttccctgagc tggattctcc ccagcttcat ttctctcttc ctacagaccc
4441 tgatcccatc agaggttttg ggtcttatca tccctctgct tactctcctt ttcattttca
4501 accttccgca gcctctttga ctgccaacct taggctgcca atggcctctg cttacctga
4561 ggctctttgc agtcagtccc ggactacccc agtagatctc tgtcttctag aagaatcagt
4621 aggcagtctc gaaggaagtc gatgtcctgt ctttgctttt caaagttctg acacagaaag
4681 tgatgagcta tcagaagtac ttcaagacag ctgcttttta caaataaaat gtgatacaaa
4741 agatgacagt atcccgtgct ttctggaagt aaaagaagag gatgaaatag tgtgcacaca
4801 acactggcag gatgctgtgc cttggacaga actcctcagt ctacagacag aggatggctt
4861 ctggaaactt acaccagaac tgggactat attaaatctt aatacaaatg gtttgcacag
4921 ctttcttaaa caaaaaggca ttcaatctct aggtgtaaaa ggaagagaat gtctcctgga
4981 cctaattgcc acaatgctgg tactacagtt tattcgcacc aggttggaaa aagagggaat
5041 agtgttcaaa tcactgatga aaatggatga cccttctatt tccaggaata ttccctgggc
5101 ttttgaggca ataaagcaag caagtgaatg ggtaagaaga actgaaggac agtacccatc
5161 tatctgccca cggcttgaac tggggaacga ctgggactct gccaccaagc agttgctggg
5221 actccagccc ataagcactg tgtcccctct tcatagagtc ctccattaca gtcaaggcta
5281 agtcaaatga aactgaattt taaacttttt gcatgcttct atgtagaaaa taatcaaatg
5341 ataatagata cttataatga aacttcatta aggtttcatt cagtgtagca attactgtct
5401 ttaaaaatta gtggaagaa gaattacttt aatcaactaa caagcaataa taaaatgaaa
5461 cttaaaat
```

```
   1 ctagaattca gcggccgctg aattctaggc ggcgcggcgg cgacggagca ccggcggcgg
  61 cagggcgaga gcattaaatg aaagcaaaag agttaataat ggcaacacgg ctccagaaga
 121 ctcttcccct gccaagaaaa ctcgtagatg ccagagacag gagtcgaaaa agatgcctgt
 181 ggctggagga aaagctaata aggacaggac agaagacaag caagatggta tgccaggaag
 241 gtcatgggcc agcaaaaggg tctctgaatc tgtgaaggcc ttgctgttaa agggcaaagc
 301 tcctgtggac ccagagtgta cagccaaggt ggggaaggct catgtgtatt gtgaaggaaa
 361 tgatgtctat gatgtcatgc taaatcagac caatctccag ttcaacaaca acaagtacta
 421 tctgattcag ctattagaag atgatgccca gaggaacttc agtgtttgga tgagatgggg
 481 ccgagttggg aaaatgggac agcacagcct ggtggcttgt tcaggcaatc tcaacaaggc
 541 caaggaaatc tttcagaaga aattccttga caaaacgaaa aacaattggg aagatcgaga
 601 aaagtttgag aaggtgcctg gaaaatatga tatgctacag atggactatg ccaccaatac
 661 tcaggatgaa gaggaaacaa aaaaagagga atctcttaaa tctcccttga agccagagtc
 721 acagctagat cttcgggtac aggagttaat aaagttgatc tgtaatgttc aggccatgga
 781 agaaatgatg atggaaatga agtataatac caagaaagcc ccacttggga agctgacagt
 841 ggcacaaatc aaggcaggtt accagtctct taagaagatt gaggattgta ttcgggctgg
 901 ccagcatgga cgagctctca tggaagcatg caatgaattc tacaccagga ttccgcatga
 961 ctttggactc cgtactcctc cactaatccg gacacagaag gaactgtcag aaaaaataca
1021 attactagag gctttgggag acattgaaat tgctattaag ctggtgaaaa cagagctaca
1081 aagcccagaa cacccattgg accaacacta tagaaaccta cattgtgcct tgcgccccct
1141 tgaccatgaa agttacgagt tcaaagtgat ttcccagtac ctacaatcta cccatgctcc
1201 cacacacagc gactatacca tgaccttgct ggatttgttt gaagtggaga aggatggtga
1261 gaaagaagcc ttcagagagg accttcataa caggatgctt ctatggcatg gttccaggat
1321 gagtaactgg gtgggaatct tgagccatgg gcttcgaatt gcccacccct aagctcccat
1381 cacaggttac atgtttggga aaggaatcta ctttgctgac atgtcttcca agagtgccaa
1441 ttactgcttt gcctctcgcc taaagaatac aggactgctg ctcttatcag aggtagctct
1501 aggtcagtgt aatgaactac tagaggccaa tcctaaggcc gaaggattgc ttcaaggtaa
1561 acatagcacc aaggggctgg gcaagatggc tcccagttct gcccacttcg tcaccctgaa
1621 tgggagtaca gtgccattag gaccagcaag tgacacagga attctgaatc cagatggtta
1681 taccctcaac tacaatgaat atattgtata taaccccaac caggtccgta tgcggtacct
1741 tttaaaggtt cagtttaatt tccttcagct gtggtgaatg ttgatcttaa ataaaccaga
1801 gatctgatct tcaagcaaga aaataagcag tgttgtactt gtgaattttg tgatatttta
1861 tgtaataaaa actgtacagg tctaaaaaaa aaaaaaaaaa aaaaaaaaaa
```
//

Figure 11

```
   1 tgggactggt cgcctgactc ggcctgcccc agcctctgct tcacccact ggtggccaaa
  61 tagccgatgt ctaatccccc acacaagctc atcccggcc tctgggattg ttgggaattc
 121 tctccctaat tcacgcctga ggctcatgga gagttgctag acctgggact gccctgggag
 181 gcgcacacaa ccaggccggg tggcagccag gacctctccc atgtccctgc ttttcttggc
 241 catggctcca aagccgaagc cctgggtaca gactgagggc cctgagaaga agaagggccg
 301 gcaggcagga agggaggagg accccttccg ctccaccgct gaggccctca aggccatacc
 361 cgcagagaag cgcataatcc gcgtggatcc aacatgtcca ctcagcagca accccgggac
 421 ccaggtgtat gaggactaca actgcaccct gaaccagacc aacatcgaga caacaacaa
 481 caagttctac atcatccagc tgctccaaga cagcaaccgc ttcttcacct gctggaaccg
 541 ctggggccgt gtgggagagg tcggccagtc aaagatcaac cacttcacaa ggctagaaga
 601 tgcaaagaag gactttgaga agaaatttcg ggaaaagacc aagaacaact gggcagagcg
 661 ggaccacttt gtgtctcacc cgggcaagta cacacttatc gaagtacagg cagaggatga
 721 ggcccaggaa gctgtggtga aggtggacag aggcccagtg aggactgtga ctaagcgggt
 781 gcagccctgc tccctggacc cagccacgca gaagctcatc actaacatct tcagcaagga
 841 gatgttcaag aacaccatgg ccctcatgga cctggatgtg aagaagatgc cctgggaaa
 901 gctgagcaag caacagattg cacggggttt cgaggccttg gaggcgctgg aggaggccct
 961 gaaaggcccc acggatggtg gccaaagcct ggaggagctg tcctcacact tttacaccgt
1021 catcccgcac aacttcggcc acagccagcc cccgcccatc aattcccctg agcttctgca
1081 ggccaagaag gacatgctgc tggtgctggc ggacatcgag ctgcccagg ccctgcaggc
1141 agtctctgag caggagaaga cggtggagga ggtgccacac ccctggacc gagactacca
1201 gcttctcaag tgccagctgc agctgctaga ctctggagca cctgagtaca aggtgataca
1261 gacctactta gaacagactg gcagcaacca caggtgccct acacttcaac acatctggaa
1321 agtaaaccaa gaaggggagg aagacagatt ccaggcccac tccaaactgg gtaatcggaa
1381 gctgctgtgg catggcacca acatggccgt ggtggccgcc atcctcacta gtgggctccg
1441 catcatgcca cattctggtg ggcgtgttgg caagggcatc tactttgcct cagagaacag
1501 caagtcagct ggatatgtta ttggcatgaa gtgtggggcc caccatgtcg gctacatgtt
1561 cctgggtgag gtggccctgg gcagagagca ccatatcaac acggacaacc ccagcttgaa
1621 gagcccacct cctggcttcg acagtgtcat tgcccgaggc cacaccgagc ctgatccgac
1681 ccaggacact gagttggagc tggatggcca gcaagtggtg gtgccccagg gccagcctgt
1741 gccctgccca gagttcagca gctccacatt ctcccagagc gagtacctca tctaccagga
1801 gagccagtgt cgcctgcgct acctgctgga ggtccacctc tgagtgcccg ccctgtcccc
1861 cggggtcctg caaggctgga ctgtgatctt caatcatcct gcccatctct ggtaccccta
1921 tatcactcct ttttttcaag aatacaatac gttgttgtta actatagtca ccatgctgta
1981 caagatccct gaacttatgc ctcctaactg aaatttttgta ttctttgaca catctgccca
2041 gtccctctcc tcccagcccca tggtaaccag catttgactc tttacttgta taagggcagc
2101 ttttataggt tccacatgta agtgagatca tgcagtgttt gtctttctgt gcctggctta
2161 tttcactcag cataatgtgc accgggttca cccatgtttt cataaatgac aagatttcct
2221 cctttaaaaa aaaaaaaaaa aaaaaaaaaa aaaaaaaaaa aaa
```

Figure 12

```
   1 cgaagatggc ggcgtcgcgt cgctctcagc atcatcacca ccatcatcaa caacagctcc
  61 agcccgcccc aggggcttca gcgccgccgc cgccacctcc tcccccactc agccctggcc
 121 tggccccggg gaccacccca gcctctccca cggccagcgg cctggccccc ttcgcctccc
 181 cgcggcacgg cctagcgctg ccggaggggg atggcagtcg ggatccgccc gacaggcccc
 241 gatccccgga cccggttgac ggtaccagct gttgcagtac caccagcaca atctgtaccg
 301 tcgccgccgc tcccgtggtc ccagcggttt ctacttcatc tgccgctggg gtcgctccca
 361 acccagccgg cagtggcagt aacaattcac cgtcgtcctc ttcttccccg acttcttcct
 421 catcttcctc tccatcctcc cctggatcga gcttggcgga gagccccgag gcggccggag
 481 ttagcagcac agcaccactg gggcctgggg cagcaggacc tgggacaggg gtcccagcag
 541 tgagcggggc cctacgggaa ctgctggagg cctgtcgcaa tggggacgtg tcccgggtaa
 601 agaggctggt ggacgcggca aacgtaaatg caaaggacat ggccggccgg aagtcttctc
 661 ccctgcactt cgctgcaggt tttggaagga aggatgttgt agaacactta ctacagatgg
 721 gtgctaatgt ccacgctcgt gatgatggag gtctcatccc gcttcataat gcctgttctt
 781 ttggccatgc tgaggttgtg agtctgttat tgtgccaagg agctgatcca aatgccaggg
 841 ataactggaa ctatacacct ctgcatgaag ctgctattaa agggaagatc gatgtgtgca
 901 ttgtgctgct gcagcacgga gctgacccaa acattcggaa cactgatggg aaatcagccc
 961 tggacctggc agatccttca gcaaaagctg tccttacagg tgaatacaag aaagacgaac
1021 tcctagaagc tgctaggagt ggtaatgaag aaaaactaat ggctttactg actcctctaa
1081 atgtgaattg ccatgcaagt gatgggcgaa agtcgactcc tttacatcta gcagcgggct
1141 acaacagagt tcgaatagtt cagcttcttc ttcagcatgg tgctgatgtt catgcaaaag
1201 acaaaggtgg acttgtgcct cttcataatg catgttcata tggacattat gaagtcacag
1261 aactgctact aaagcatgga gcttgtgtta atgccatgga tctctggcag tttactccac
1321 tgcacggggc tgcttccaag aaccgtgtag aagtcgtctc tttgttactt agccatggcg
1381 ctgatcctac gttagtcaac tgccatggca aaagtgctgt ggatatggct ccaactccgg
1441 agcttaggga gagattgact tatgaattta aaggtcattc tttactacaa gcagccagag
1501 aagcagactt agctaaagtt aaaaaaacac tcgctctgga aatcattaat ttcaaacaac
1561 cgcagtctca tgaaacagca ctgcactgtg ctgtggcctc tctgcatccc aaacgtaaac
1621 aagtgacaga attgttactt agaaaaggag caaatgttaa tgaaaaaaat aaagatttca
1681 tgactcccct gcatgttgca gccgaaagac cccataatga tgtcatggaa gttctgcata
1741 agcatggcgc caagatgaat gcactggaca cccttggtca gactgctttg catagagccg
1801 ccctagcagg ccacctgcag acctgccgcc tcctgctgag ttacggctct gacccctcca
1861 tcatctcctt acaaggcttc acagcagcac agatgggcaa tgaagcagtg cagcagattc
1921 tgagtgtgag ttacggctct gacccctcca tcatctcctt acaaggcttc acagcagcac
1981 agatgggcaa tgaagcagtg cagcagattc tgagtggtca ttcgtagata gtgatcattc
2041 tacttcagcc ttaatggtga tcttgagacg ggaagattta gaaggaaatc tatccagcat
2101 gtcttcactg tcaacatgaa gagtacacct atacgtactt ctgatgttga ttatcgactc
2161 ttagaggcat ctaaagctgg agacttggaa actgtgaagc aactttgcag ctctcaaaat
2221 gtgaattgta gagacttaga gggccggcat tccacgccct tacacttcgc agcaggctac
2281 aacagagtac acctatacgt acttctgatg ttgattatcg actcttagag gcatctaaag
2341 ctggagactt ggaaactgtg aagcaacttt gcagctctca aaatgtgaat tgtagagact
2401 tagagggccg gcattccacg cccttacact tcgcagcagg ctacaaccgc gtgtctgttg
2461 tagagtacct gctacaccac ggtgccgatc tccatgccaa agacaagggt gccttggtgc
2521 cccttcataa tgcctgttca tatgcgacact atgaggtggc tgagcttttca gtaaggcatg
2581 gggcttctgt caatgtggcg gacttatgga aatttacccc tctccatgaa gcagcagcta
2641 aggaaagta tgaaatctgc aagctccttt taaaacatgg agcagatcca actaaaaaga
2701 acagagatgg aaatacacct ttggatttgg taaaggaagg agacacagat attcaggact
2761 tactgaaagg ggatgctgct ttgttggatg ctgccaagaa gggctgcctg gcaagagtgc
2821 agaagctctg taccccagag aatatcaact gcagagacc ccagggcaga aattcaaccc
2881 ctctgcacct ggcagcaggc tataataacc tggaagtagc tgaatatctt ctagagcatg
2941 gagctgatgt taatgcccag gacaagggtg gtttaattcc tcttcataat gcggcatctt
3001 atgggcatgt tgacatagcg gctttattga taaaatacaa cacgtgtgta aatgcaacag
3061 ataagtgggc gtttactccc ctccatgaag cagcccagaa aggaaggacg cagctgtgcg
3121 ccctcctcct agcgcatggt gcagacccca ccatgaagaa ccaggaaggc cagacgcctc
3181 tggatctggc aacagctgac gatatcagag ctttgctgat agatgccatg cccccagagg
3241 ccttacctac ctgtttttaaa cctcaggcta ctgtagtgag tgcctctctg atctcaccag
3301 catccaccc ctcctgcctc tcggctgcca gcagataga caacctcact ggccctttag
3361 cagagttggc cgtaggagga gcctccaatg caggggatgg cgccgcggga acagaaagga
3421 aggaaggaga agttgctggt cttgacatga atatcagcca atttctaaaa agccttggcc
3481 ttgaacacct tcgggtatatc tttgaaacag aacagattac actagatgtg ttggctgata
3541 tgggtcatga agagttgaaa gaaataggca tcaatgcata tgggcaccgc cacaaattaa
3601 tcaaaggagt agaaagactc ttaggtggac aatccttat ttgactttc
3661 actgtgttaa tcagggaacg attttgctgg atcttgctcc agaagataaa gaatatcagt
3721 cagtggaaga agagatgcaa agtactattc gagaacacag agatggtggt aatgctggcg
3781 gcatcttcaa cagatacaat gtcattcgaa ttcaaaaagt tgtcaacaag aagttgaggg
3841 agcggttctg ccaccgacag aaggaagtgt ctgaggagaa tcacaaccat cacaatgagc
```

```
3901 gcatgttgtt tcatggttct cctttcatta atgccattat tcataaaggg tttgatgagc
3961 gacatgcata cataggagga atgtttgggg ccgggattta ttttgctgaa aactcctcaa
4021 aaagcaacca atatgtttat ggaattggag gaggaacagg ctgccctaca cacaaggaca
4081 ggtcatgcta tatatgtcac agacaaatgc tcttctgtag agtgacoctt gggaaatcct
4141 ttctgcagtt tagcaccatg aaaatggccc acgcgcctcc agggcaccac tcagtcattg
4201 gtagaccgag cgtcaatggg ctggcatatg ctgaatatgt catctacaga ggagaacagg
4261 catcccaga gtatcttatc acttaccaga tcatgaagcc agaagcccct tcccagaccg
4321 caacagccgc agagcagaag acctagtgaa tgcctgctgg tgaaggccag atcagatttc
4381 aacctgggac tggattacag aggattgttt ctaataacaa catcaatatt ctagaagtcc
4441 ctgacagcct agaaataagc tgtttgtctt ctataaagca ttgctatagt g
```

```
   1 cgcgccgcct cgctagccga aacctgccca gccggtgccc ggccactgcg cacgcgcggg
  61 acgacgtcac gtgcgctccc ggggctggac ggagctggca ggaggggcct tgccagcttc
 121 cgccgccgcg tcgtttcagg acccggacgg cggattcgcg ctgcctccgc cgccgcgggg
 181 cagccggggg gcagggagcc cagcgagggg cgcgcgtggg cgcggccatg ggactgcgcc
 241 ggatccggtg acagcaggga gccaagcggc ccgggccctg agcgcgtctt ctccgggggg
 301 cctcgccctc ctgctcgcgg ggccggggct cctgctccgg ttgctggcgc tgttgctggc
 361 tgtggcggcg gccaggatca tgtcgggtcg ccgctgcgcc ggcggggggag cggcctgcgc
 421 gagcgccgcg gccgaggccg tggagccggc cgcccgagag ctgttcgagg cgtgccgcaa
 481 cggggacgtg gaacgagtca agaggctggt gacgcctgag aaggtgaaca gccgcgacac
 541 ggcgggcagg aaatccaccc cgctgcactt cgccgcaggt tttgggcgga aagacgtagt
 601 tgaatatttg cttcagaatg gtgcaaatgt ccaagcacgt gatgatgggg gcttattcc
 661 tcttcataat gcatgctctt ttggtcatgc tgaagtagtc aatctccttt tgcgacatgg
 721 tgcagacccc aatgctcgag ataattggaa ttatactcct ctccatgaag ctgcaattaa
 781 aggaaagatt gatgtttgca ttgtgctgtt acagcatgga gctgagccaa ccatccgaaa
 841 tacagatgga aggacagcat tggatttagc agatccatct gccaaagcag tgcttactgg
 901 tgaatataag aaagatgaac tcttagaaag tgccaggagt ggcaatgaag aaaaaatgat
 961 ggctctactc acaccattaa atgtcaactg ccacgcaagt gatggcagaa agtcaactcc
1021 attacatttg gcagcaggat ataacagagt aaagattgta cagctgttac tgcaacatgg
1081 agctgatgtc catgctaaag ataaaggtga tctggtacca ttacacaatg cctgttctta
1141 tggtcattat gaagtaactg aacttttggt caagcatggt gcctgtgtaa atgcaatgga
1201 cttgtggcaa ttcactcctc ttcatgaggc agcttctaag aacagggttg aagtatgttc
1261 tcttctctta agttatggtg cagacccaac actgctcaat tgtcacaata aagtgctat
1321 agacttggct cccacaccac agttaaaaga aagattagca tatgaattta aaggccactc
1381 gttgctgcaa gctgcacgag aagctgatgt tactcgaatc aaaaaacatc tctctctgga
1441 aatggtgaat tcaagcatc ctcaaacaca tgaaacagca ttgcattgtg ctgctgcatc
1501 tccatatccc aaaagaaagc aaatatgtga actgttgcta agaaaaggag caaacatcaa
1561 tgaaaagact aaagaattct tgactcctct gcacgtggca tctgagaaag ctcataatga
1621 tgttgttgaa gtagtggtga acatgaagc aaaggttaat gctctggata atcttggtca
1681 gacttctcta cacagagctg catattgtgg tcatctacaa acctgccgcc tactcctgag
1741 ctatggggtgt gatcctaaca ttatatccct tcagggcttt actgctttac agatgggaaa
1801 tgaaaatgta cagcaactcc tccaagaggg tatctcatta ggtaattcag aggcagacag
1861 acaattgctg gaagctgcaa aggctggaga tgtcgaaact gtaaaaaaac tgtgtactgt
1921 tcagagtgtc aactgcagag acattgaagg gcgtcagtct acaccacttc attttgcagc
1981 tgggtataac agagtgtccg tggtggaata tctgctacag catggagctg atgtgcatgc
2041 taaagataaa ggaggccttg taccttttgca caatgcatgt tcttatggac attatgaagt
2101 tgcagaactt cttgttaaac atggagcagt agttaatgta gctgatttat ggaaatttac
2161 acctttacat gaagcagcag caaaaggaaa atatgaaatt tgcaaacttc tgctccagca
2221 tggtgcagac cctacaaaaa aaaacaggga tggaaatact cctttggatc ttgttaaaga
2281 tggagataca gatattcaag atctgctag gggagatgca gctttgctag atgctgccaa
2341 gaagggttgt ttagccagag tgaagaagtt gtcttctcct gataatgtaa attgccgcga
2401 tacccaaggc agacattcaa caccttaca tttagcagct ggtataata atttagaagt
2461 tgcagagtat ttgttacaac acggagctga tgtgaatgcc caagacaaag gaggacttat
2521 tccttttacat aatgcagcat cttacgggca tgtagatgta gcagctctac taataaagta
2581 taatgcatgt gtcaatgcca cggacaaatg ggcttttcaca cctttgcacg aagcagccca
2641 aaagggacga acacagcttt gtgctttgtt gctagcccat ggagctgacc cgactcttaa
2701 aaatcaggaa ggacaaacac ctttagattt agtttcagca gatgatgtca gcgctcttct
2761 gacagcagcc atgcccccat ctgctctgcc ctcttgttac aagcctcaag tgctcaatgg
```

```
2821 tgtgagaagc ccaggagcca ctgcagatgc tctctcttca ggtccatcta gcccatcaag
2881 cctttctgca gccagcagtc ttgacaactt atctgggagt ttttcagaac tgtcttcagt
2941 agttagttca agtggaacag agggtgcttc cagtttggag aaaaaggagg ttccaggagt
3001 agattttagc ataactcaat tcgtaaggaa tcttggactt gagcacctaa tggatatatt
3061 tgagagagaa cagatcactt tggatgtatt agttgagatg gggcacaagg agctgaagga
3121 gattggaatc aatgcttatg gacataggca caaactaatt aaaggagtcg agagacttat
3181 ctccggacaa caaggtctta acccatattt aactttgaac acctctggta gtggaacaat
3241 tcttatagat ctgtctcctg atgataaaga gtttcagtct gtggaggaag agatgcaaag
3301 tacagttcga gagcacagag atggaggtca tgcaggtgga atcttcaaca gatacaatat
3361 tctcaagatt cagaaggttt gtaacaagaa actatgggaa agatacactc accggagaaa
3421 agaagtttct gaagaaaacc acaaccatgc caatgaacga atgctatttc atgggtctcc
3481 ttttgtgaat gcaattatcc acaaaggctt tgatgaaagg catgcgtaca taggtggtat
3541 gtttggagct ggcatttatt ttgctgaaaa ctcttccaaa agcaatcaat atgtatatgg
3601 aattggagga ggtactgggt gtccagttca caagacaga tcttgttaca tttgccacag
3661 gcagctgctc ttttgccggg taaccttggg aaagtctttc ctgcagttca gtgcaatgaa
3721 aatggcacat tctcctccag gtcatcactc agtcactggt aggcccagtg taaatggcct
3781 agcattagct gaatatgtta tttacagagg agaacaggct tatcctgagt atttaattac
3841 ttaccagatt atgaggcctg aaggtatggt cgatggataa atagttattt taagaaacta
3901 attccactga acctaaaatc atcaaagcag cagtggcctc tacgttttac tcctttgctg
3961 aaaaaaaatc atcttgccca caggcctgtg gcaaaaggat aaaaatgtga acgaagttta
4021 acattctgac ttgataaagc tttaataatg tacagtgttt tctaaatatt tcctgttttt
4081 tcagcacttt aacagatgcc attccaggtt aaactgggtt gtctgtacta aattataaac
4141 agagttaact tgaaccttt atatgttatg cattgattct aacaaactgt aatgccctca
4201 acagaactaa ttttactaat acaatactgt gttctttaaa acacagcatt tacactgaat
4261 acaatttcat ttgtaaaact gtaaataaga gcttttgtac tagcccagta tttatttaca
4321 ttgctttgta atataaatct gttttagaac tgcagcggtt tacaaaattt tttcatatgt
4381 attgttcatc tatacttcat cttacatcgt catgattgag tgatctttac atttgattcc
4441 agaggctatg ttcagttgtt agttgggaaa gattgagtta tcagatttaa tttgccgatg
4501 ggagcctttc tctgtcatta gaaatctttc tcatttaaga acttatgaat atgctgaaga
4561 tttaatttgt gatacctttg tatgtatgag acacattcca aagagctcta actatgatag
4621 gtcctgatta ctaaagaagc ttctttactg gcctcaattt ctagcttttca tgttggaaaa
4681 ttttctgcag tccttctgtg aaaattagag caaagtgctc ctgttttta gagaaactaa
4741 atcttgctgt tgaacaatta ttgtgttctt ttcatggaac ataagtagga tgttaacatt
4801 tccagggtgg gaagggtaat cctaaatcat ttcccaatct attctaatta ccttaaatct
4861 aaaggggaaa aaaaaaatca caaacaggac tgggtagttt tttatcctaa gtatatttt
4921 tcctgttctt tttacttggt tttattgctg tatttatagc caatctatac atcatgggta
4981 aacttaaccc agaactataa aatgtagttg tttcagtccc cttcaggcct cctgaatggg
5041 caagtgcagt gaaacaggtg cttcctgctc ctgggttttc tctccatgat gttatgccca
5101 attggaaata tgctgtcagt ttgtgcacca tatggtgacc acgcctgtgc tcagtttggc
5161 agctatagaa ggaaatgctg tcccataaaa tgccatccct atttctaata taacactctt
5221 ttccaggaag catgcttaag catcttgtta cagagacata catccattat ggcttggcaa
5281 tctcttttat ttgttgactc tagctccctt caaagtcgag gaaagatctt tactcactta
5341 atgaggacat tccccatcac tgtctgtacc agttcacctt tattttacgt tttattcagt
5401 ctgtaaatta actggcccct tgcagtaact tgtacataaa gtgctagaaa atcatgttcc
5461 ttgtcctgag taagagttaa tcagagtaag tgcatttctg gagttgtttc tgtgatgtaa
5521 attatgatca ttatttaaga agtcaaatcc tgatcttgaa gtgcttttta tacagctctc
5581 taataattac aaatatccga aagtcatttc ttggaacaca agtggagtat gccaaatttt
5641 atatgaattt ttcagattat ctaagcttcc aggttttata attagaaagat aatgagagaa
5701 ttaatgggggt ttatatttac attatctctc aactatgtag cccatattac tcaccctatg
5761 agtgaatctg gaattgcttt tcatgtgaaa tcattgtggt ctatgagttt acaatactgc
```

Figure 13 (continued)

5821 aaactgtgtt attttatcta aaccattgct taatgagtgt gttttt ccat gaatgaatat
5881 accgtggttc atatgttagc atggcagcat tttcagatag cttttt gttt gttgggaagt
5941 tggggttttg gggggagggg gagtattagt acgttgcatg gaatagccta ctttataatg
6001 atgggaatgc ttttt ctttt gttttgggat ttttttttt gaagtgaaat ttaacttttt
6061 gtgccagtag tactattata cccatcttca gtgtcttact tgtactgtat caaattccat
6121 accctcattt aattcttaat aaaactgttc acttgtaaaa aaaaaaaaaa aaaaaaaaa
6181 aaaaaaaaa Figure 13 (continued)

Figure 14

```
   1 cgcccgccca gccccggggg cagggaaagc ctaaattacg gaattaccgc gagcaaggag
  61 cgcggaatcg gggagcgtcc ggagctagct ggatcctcta ggcaggatgg tgatgggaat
 121 ctttgcaaat tgtatcttct gtttgaaagt gaagtactta cctcagcagc agaagaaaaa
 181 gctacaaact gacattaagg aaaatggcgg aaagttttcc ttttcgttaa atcctcagtg
 241 cacacatata atcttagata atgctgatgt tctgagtcag taccaactga attctatcca
 301 aaagaaccac gttcatattg caaacccaga ttttatatgg aaatctatca gagaaaagag
 361 actcttggat gtaaagaatt atgatcctta taagcccctg gacatcacac cacctcctga
 421 tcagaaggcg agcagttctg aagtgaaaac agaaggtcta tgcccggaca gtgccacaga
 481 ggaggaagac actgtggaac tcactgagtt tggtatgcag aatgttgaaa ttcctcatct
 541 tcctcaagat tttgaagttg caaaatataa caccttggag aaagtgggaa tggagggagg
 601 ccaggaagct gtggtggtgg agcttcagtg ttcgcgggac tccagggact gtcctttcct
 661 gatatcctca cacttcctcc tggatgatgg catggagact agaagacagt ttgctataaa
 721 gaaaacctct gaagatgcaa gtgaatactt tgaaaattac attgaagaac tgaagaaaca
 781 aggatttcta ctaagagaac atttcacacc tgaagcaacc caattagcat ctgaacaatt
 841 gcaagcattg cttttggagg aagtcatgaa ttcaagcact ctgagccaag aggtgagcga
 901 tttagtagag atgatttggg cagaggccct gggccacctg gaacacatgc ttctcaagcc
 961 agtgaacagg attagcctca acgatgtgag caaggcagag gggattctcc ttctagtaaa
1021 ggcagcactg aaaaatggag aaacagcaga gcaattgcaa aagatgatga cagagttta
1081 cagactgata cctcacaaag gcacaatgcc caaagaagtg aacctgggac tattggctaa
1141 gaaagcagac ctctgccagc taataagaga catggttaat gtctgtgaaa ctaatttgtc
1201 caaacccaac ccaccatccc tggccaaata ccgagctttg aggtgcaaaa ttgagcatgt
1261 tgaacagaat actgaagaat ttctcagggt tagaaaaagag gttttgcaga atcatcacag
1321 taagagccca gtggatgtct tgcagatatt tagagttggc agagtgaatg aaaccacaga
1381 gttttgagc aaacttggta atgtgaggcc cttgttgcat ggttctcctg tacaaaaacat
1441 cgtgggaatc ttgtgtcgag ggttgctttt acccaaagta gtggaagatc gtggtgtgca
1501 aagaacagac gtcggaaacc ttggaagtgg gatttatttc agtgattcgc tcagtacaag
1561 tatcaagtac tcacacccgg gagagacaga tggcaccaga ctcctgctca tttgtgacgt
1621 agccctcgga aagtgtatgg acttacatga gaaggacttt cccttaactg aagcaccacc
1681 aggctacgac agtgtgcatg gagtttcaca aacagcctct gtcaccacag actttgagga
1741 tgatgaattt gttgtctata aaaccaatca ggttaaaatg aaatatatta ttaaatttc
1801 catgcctgga gatcagataa aggactttca tcctagtgat catactgaat tagaggaata
1861 cagacctgag ttttcaaatt tttcaaaggt tgaagattac cagttaccag atgccaaaac
1921 ttccagcagc accaaggccg gcctccagga tgcctctggg aacttggttc ctctggagga
1981 tgtccacatc aaagggagaa tcatagacac tgtagcccag gtcattgttt ttcagacata
2041 cacaaataaa agtcacgtgc ccattgaggc aaaatatatc tttcctttgg atgacaaggc
2101 cgctgtgtgt ggcttcgaag ccttcatcaa tgggaagcac atagttggag agattaaaga
2161 gaaggaagaa gcccagcaag agtacctaga agccgtgacc cagggccatg gcgcttacct
2221 gatgagtcag gatgctccgg acgtttttac tgtaagtgtt ggaaacttac cccctaaggc
2281 taaggttctt ataaaaatta cctacatcac agaactcagc atcctgggca ctgttggtgt
2341 ctttttcatg cccgccaccg tagcaccctg gcaacaggac aaggcttga atgaaaaacct
2401 tcaggataca gtagagaaga tttgtataaa agaaatagga acaaagcaaa gcttctcttt
2461 gactatgtct attgagatgc cgtatgtgat tgaattcatt ttcagtgata cacatgaact
2521 gaaacaaaag cgcacagact gcaaagctgt cattagcacc atggaaggca gctccttaga
2581 cagcagtgga ttttctctcc acatcggttt gtctgctgcc tatctcccaa gaatgtgggt
2641 tgaaaaacat ccagaaaaag aaagcgaggc ttgcatgctt gtctttcaac ccgatctcga
2701 tgtcgacctc cctgacctag ccagtgagag cgaagtgatt atttgtcttg actgctccag
```

```
2761 ttccatggag ggtgtgacat tcttgcaagc caagcaaatc accttgcatg cgctgtcctt
2821 ggtgggtgag aagcagaaag taaatattat ccagttcggc acaggttaca aggagctatt
2881 ttcgtatcct aagcatatca caagcaatac cacggcagca gagttcatca tgtctgccac
2941 acctaccatg gggaacacag acttctggaa aacactccga tatcttagct tattgtaccc
3001 tgctcgaggg tcacggaaca tcctcctggt gtctgatggg cacctccagg atgagagcct
3061 gacattacag ctcgtgaaga ggagccgccc gcacaccagg ttattcgcct gcggtatcgg
3121 ttctacagca aatcgtcacg tcttaaggat tttgtcccag tgtggtgccg gagtatttga
3181 atattttaat gcaaaatcca agcatagttg gagaaaacag atagaagacc aaatgaccag
3241 gctatgttct ccgagttgcc actctgtctc cgtcaaatgg cagcaactca atccagatgc
3301 gcccgaggcc ctgcaggccc cagcccaggt gccatccttg tttcgcaatg atcgactcct
3361 tgtctatgga ttcattcctc actgcacaca agcaactctg tgtgcactaa ttcaagagaa
3421 agaattttgt acaatggtgt cgactactga gcttcagaag acaactggaa ctatgatcca
3481 caagctggca gcccgagctc taatcagaga ttatgaagat ggcattcttc acgaaaatga
3541 aaccagtcat gagatgaaaa aacaaaacctt gaaatctctg attattaaac tcagtaaaga
3601 aaactctctc ataacacaat ttacaagctt tgtggcagtt gagaaaaggg atgagaatga
3661 gtcgcctttt cctgatattc caaaagtttc tgaacttatt gccaagaag atgtagactt
3721 cctgccctac atgagctggc aggggggagcc ccaagaagcc gtcaggaacc agtctctttt
3781 agcatcctct gagtggccag aattacgttt atccaaacga aaacatagga aaattccatt
3841 ttccaaaaga aaaatggaat tatctcagcc agaagttct gaagatttg aagaggatgg
3901 cttaggtgta ctaccagctt tcacatcaaa tttggaacgt ggaggtgtgg aaaagctatt
3961 ggatttaagt tggacagagt catgtaaacc aacagcaact gaaccactat taagaaagt
4021 cagtccatgg gaaacatcta cttctagctt ttttcctatt ttggctccgg ccgttggttc
4081 ctatcttacc ccgactaccc gcgctcacag tcctgcttcc ttgtcttttg cctcatatcg
4141 tcaggtagct agtttcggtt cagctgctcc tcccagacag tttgatgcat ctcaattcag
4201 ccaaggccct gtgcctggca cttgtgctga ctggatccca cagtcggcgt cttgtcccac
4261 aggacctccc cagaacccac cttctgcacc ctattgtggc attgttttt cagggagctc
4321 attaagctct gcacagtctg ctccactgca acatcctgga ggctttacta ccaggccttc
4381 tgctggcacc ttccctgagc tggattctcc ccagcttcat ttctctcttc ctacagaccc
4441 tgatcccatc agaggttttg ggtcttatca tccctctgct tactctcctt ttcattttca
4501 accttcgcca gcctctttga ctgccaacct taggctgcca atggcctctg cttttacctga
4561 ggctctttgc agtcagtccc ggactacccc agtagatctc tgtcttctag aagaatcagt
4621 aggcagtctc gaaggaagtc gatgtcctgt ctttgctttt caaagttctg acacagaaag
4681 tgatgagcta tcagaagtac ttcaagacag ctgcttttta caaataaagt gtgatacaaa
4741 agatgacagt atcccgtgct ttctggaatt aaaagaagag gatgaaatag tgtgcacaca
4801 acactggcag gatgctgtgc cttggacaga actcctcagt ctacagacag aggatggctt
4861 ctggaaaactt acaccagaac tgggacttat attaaatctt aatacaaatg gtttgcacag
4921 cttttctaaa caaaaaggca ttcaatctct aggtgtaaaa ggaagagaat gtctcctgga
4981 cctaattgcc acaatgctgg tactacagtt tattcgcacc aggttggaaa aagagggaat
5041 agtgttcaaa tcactgatga aaatggatga cccttctatt tccaggaata ttccctgggc
5101 ttttgaggca ataaagcaag caagtgaatg ggtaagaaga actgaaggac agtaccccatc
5161 tatctgccca cggcttgaac tggggaacga ctgggactct gccaccaagc agttgctggg
5221 actccagccc ataagcactg tgtcccctct tcatagagtc ctccattaca gtcaaggcta
5281 agtcaaatga aactgaattt taaacttttt gcatgcttct atgtagaaaa taatcaaatg
5341 ataatagata attataatga aacttcatta aggtttcatt cagtgtagca attactgtct
5401 ttaaaaatta agtggaagaa gaattacttt aatcaactaa caagcaataa taaatgaaa
5461 cttaaaataa aaaaaaaaaa aaaaaaaaa
```

Figure 14 (continued)

SEQUENCE LISTING

```
<160> NUMBER OF SEQ ID NOS: 9

<210> SEQ ID NO 1
<211> LENGTH: 21
<212> TYPE: RNA
<213> ORGANISM: Homo sapiens

<400> SEQUENCE: 1
aaaagccaug guggaguaug a                                              21

<210> SEQ ID NO 2
<211> LENGTH: 23
<212> TYPE: RNA
<213> ORGANISM: Homo sapiens

<400> SEQUENCE: 2
aagaccaauc ucuccaguuc aac                                            23

<210> SEQ ID NO 3
<211> LENGTH: 21
<212> TYPE: RNA
<213> ORGANISM: Homo sapiens

<400> SEQUENCE: 3
aagaccaaca ucgagaacaa c                                              21

<210> SEQ ID NO 4
<211> LENGTH: 5468
<212> TYPE: DNA
<213> ORGANISM: Homo sapiens

<400> SEQUENCE: 4
cgcccgccca gccccggggg cagggaaagc ctaaattacg gaattaccgc gagcaaggag      60
cgcggaatcg gggagcgtcc ggagctagct ggatcctcta ggcaggatgg tgatgggaat     120
ctttgcaaat tgtatcttct gtttgaaagt gaagtactta cctcagcagc agaagaaaaa     180
gctacaaact gacattaagg aaaatggcgg aaagttttcc ttttcgttaa atcctcagtg     240
cacacatata atcttagata atgctgatgt tctgagtcag taccaactga attctatcca     300
aaagaaccac gttcatattg caaacccaga ttttatatgg aaatctatca gagaaaagag     360
actcttggat gtaaagaatt atgatcctta taagcccctg gacatcacac cacctcctga     420
```

```
tcagaaggcg agcagttctg aagtgaaaac agaaggtcta tgcccggaca gtgccacaga    480
ggaggaagac actgtggaac tcactgagtt tggtatgcag aatgttgaaa ttcctcatct    540
tcctcaagat tttgaagttg caaaatataa caccttggag aaagtgggaa tggagggagg    600
ccaggaagct gtggtggtgg agcttcagtg ttcgcgggac tccagggact gtcctttcct    660
gatatcctca cacttcctcc tggatgatgg catggagact agaagacagt ttgctataaa    720
gaaaacctct gaagatgcaa gtgaatactt tgaaaattac attgaagaac tgaagaaaca    780
aggatttcta ctaagagaac atttcacacc tgaagcaacc caattagcat ctgaacaatt    840
gcaagcattg cttttggagg aagtcatgaa ttcaagcact ctgagccaag aggtgagcga    900
tttagtagag atgatttggg cagaggccct gggccacctg aacacatgc ttctcaagcc     960 agtgaacagg attagcctca cgatgtgag caaggcagag gggattctcc ttctagtaaa    1020
ggcagcactg aaaaatggag aaacagcaga gcaattgcaa aagatgatga cagagtttta    1080
cagactgata cctcacaaag gcacaatgcc caaagaagtg aacctgggac tattggctaa    1140
gaaagcagac ctctgccagc taataagaga catggttaat gtctgtgaaa ctaatttgtc    1200
caaacccaac ccaccatccc tggccaaata ccgagctttg aggtgcaaaa ttgagcatgt    1260
tgaacagaat actgaagaat tctctcaggggt tagaaaagag gttttgcaga atcatcacag   1320
taagagccca gtggatgtct tgcagatatt tagagttggc agagtgaatg aaaccacaga    1380 gttttttgagc aaacttggta atgtgaggcc cttgttgcat ggttctcctg tacaaaacat    1440
cgtgggaatc ttgtgtcgag ggttgctttt acccaaagta gtggaagatc gtggtgtgca    1500
aagaacagac gtcggaaacc ttggaagtgg gatttatttc agtgattcgc tcagtacaag    1560
tatcaagtac tcacacccgg gagagacaga tggcaccaga ctcctgctca tttgtgacgt    1620
agccctcgga aagtgtatgg acttacatga gaaggacttt tccttaactg aagcaccacc    1680
aggctacgac agtgtgcatg gagtttcaca aacagcctct gtcaccacag actttgagga    1740
tgatgaattt gttgtctata aaaccaatca ggttaaaatg aaatatatta ttaaattttc    1800
catgcctgga gatcagataa aggactttca tcctagtgat catactgaat tagaggaata    1860
cagacctgag ttttcaaatt tttcaaaggt tgaagattac cagttaccag atgccaaaac    1920
ttccagcagc accaaggccg gcctccagga tgcttctggg aacttggttc ctctggagga    1980
tgtccacatc aaagggagaa tcatagacac tgtagcccag tcattgtttt tcagacata     2040 cacaaataaa agtcacgtgc ccattgaggc aaaatatatc tttcctttgg atgacaaggc    2100
cgctgtgtgt ggcttcgaag ccttcatcaa tgggaagcac atagtggag agattaaaga    2160 gaaggaagaa gcccagcaag agtacctaga agccgtgacc cagggccatg cgcttacct     2220 gatgagtcag gatgctccgg acgtttttac tgtaagtgtt ggaaacttac ccctaaggc    2280 taaggttctt ataaaaatta cctacatcac agaactcagc atcctgggca ctgttggtgt    2340 cttttttcatg cccgccaccg tagcaccctg caacaggac aaggctttga atgaaaacct    2400
tcaggataca gtagagaaga tttgtataaa agaaatagga acaaagcaaa gcttctcttt    2460
gactatgtct attgagatgc cgtacgtgat tgaattcatt tcagtgata ctcatgaact    2520 gaaacaaaag cgcacagact gcaaagctgt cattagcacc atggaaggca gctccttaga    2580
cagcagtgga ttttctctcc acatcggttt gtctgctgcc tatctcccaa gaatgtgggt    2640
tgaaaaacat ccgaaaaaag aaagcgaggc ttgcatgctt gtctttcaac ccgatctcga    2700
tgtcgacctc cctgacctag ccaatgagag cgaagtgatt atttgtcttg actgctccag    2760
```

```
ttccatggag ggtgtgacat tcttgcaagc caaggaaatc gccttgcatg cgctgtcctt    2820
ggtgggtgag aagcagaaag taaatattat ccagttcggc acaggttaca aggagctatt    2880
ttcgtatcct aagcatatca caagcaatac cgcggcagca gagttcatca tgtctgccac    2940
acctaccatg gggaacacag acttctggaa aacactccga tatcttagct tattgtaccc    3000
tgctcgaggg tcacggaaca tcctcctggt gtctgatggg cacctccagg atgagagcct    3060
gacattacag ctcgtgaaga ggagccgccc gcacaccagg ttattcgcct gcggtatcgg    3120
ttctacagca aatcgtcacg tcttaaggat tttgtcccag tgtggtgccg gagtatttga    3180
atattttaat gcaaaatcca agcatagttg gagaaaacag atagaagacc aaatgaccag    3240
gctatgttct ccgagttgcc actctgtctc cgtcaaatgg cagcaactca atccagatgc    3300
gcccgaggcc ctgcaggccc cagcccaggt gccatccttg tttcgcaatg atcgactcct    3360
tgtctatgga ttcattcctc actgcacaca ggcaactctg tgtgcactaa ttcaagagaa    3420
agaattttgt acaatggtgt cgactactga gcttcagaag acaactggaa ctatgatcca    3480
caagctggca gcccgagctc taatcagaga ttatgaagat ggcattcttc acgaaaatga    3540
aaccagtcat gagatgaaaa acaaaacctt gaaatctctg attattaaac tcagtaaaga    3600
aaactctctc ataacacaat ttacaagctt tgtggcagtt gagaaaaggg atgagaatga    3660
gtcacctttt cctgatattc caaaagtttc tgaacttatt gccaagaag atgtagactt    3720 cctgccctac atgagctggc aggggaacc ccaagaagcc gtcaggaacc agtctctttt    3780
agcatcctct gagtggccag aattacgttt atccaaacga aaacatagga aaattccatt    3840
ttccaaaaga aaaatggaat tatctcagcc agaagtttct gaagattttg aagaggatgc    3900
cttaggtgta ctaccagctt tcacatcaaa tttggaacgt ggacgtgtgg aaaagctatt    3960
ggatttaagt tggacagagt catgtaaacc aacagcaact gaaccactat ttaagaaagt    4020
cagtccatgg gaaacatcta cttctagctt ttttcctatt ttggctccgg ccgttggttc    4080
ctatcttacc ccgactaccc gcgctcacag tcctgcttcc ttgtcttttg cctcatatcg    4140
tcaggtagct agtttcggtt cagctgctcc tcccagacag tttgatgcat ctcaattcag    4200
ccaaggccct gtgcctggca cttgtgctga ctggatccca cagtcggcgt cttgtcccac    4260
aggacctccc cagaacccac cttctgcacc ctattgtggc attgtttttt cagggagctc    4320
attaagctct gcacagtctg ctccactgca acatcctgga ggctttacta ccaggccttc    4380
tgctggcacc ttccctgagc tggattctcc ccagcttcat ttctctcttc ctacagaccc    4440
tgatcccatc agaggttttg ggtcttatca tccctctgct tactctcctt ttcatttca    4500 accttccgca gcctctttga ctgccaacct taggctgcca atggcctctg ctttacctga    4560
ggctctttgc agtcagtccc ggactacccc agtagatctc tgtcttctag aagaatcagt    4620
aggcagtctc gaaggaagtc gatgtcctgt ctttgctttt caaagttctg acacagaaag    4680
tgatgagcta tcagaagtac ttcaagacag ctgcttttta caaataaaat gtgatacaaa    4740
agatgacagt atcccgtgct ttctggaagt aaaagaagag gatgaaatag tgtgcacaca    4800
acactggcag gatgctgtgc cttggacaga actcctcagt ctacagacag aggatggctt    4860
ctggaaactt acaccagaac tgggacttat attaaatctt aatacaaatg gtttgcacag    4920 cttttcttaaa caaaaaggca ttcaatctct aggtgtaaaa ggaagagaat gtctcctgga    4980
cctaattgcc acaatgctgg tactacagtt tattcgcacc aggttggaaa agagggaat    5040 agtgttcaaa tcactgatga aaatggatga cccttctatt tccaggaata ttccctgggc    5100
ttttgaggca ataaagcaag caagtgaatg ggtaagaaga actgaaggac agtacccatc    5160
```

| | | |
|---|---|---|
| tatctgccca cggcttgaac tggggaacga ctgggactct gccaccaagc agttgctggg | 5220 |
| actccagccc ataagcactg tgtcccctct tcatagagtc ctccattaca gtcaaggcta | 5280 |
| agtcaaatga aactgaattt taaacttttt gcatgcttct atgtagaaaa taatcaaatg | 5340 |
| ataatagata cttataatga aacttcatta aggtttcatt cagtgtagca attactgtct | 5400 |
| ttaaaaatta agtggaagaa gaattacttt aatcaactaa caagcaataa taaaatgaaa | 5460 |
| cttaaaat | 5468 |

<210> SEQ ID NO 5
<211> LENGTH: 1910
<212> TYPE: DNA
<213> ORGANISM: Homo sapiens

<400> SEQUENCE: 5

| | | |
|---|---|---|
| ctagaattca gcggccgctg aattctaggc ggcgcggcgg cgacggagca ccggcggcgg | 60 |
| cagggcgaga gcattaaatg aaagcaaaag agttaataat ggcaacacgg ctccagaaga | 120 |
| ctcttcccct gccaagaaaa ctcgtagatg ccagagacag gagtcgaaaa agatgcctgt | 180 |
| ggctggagga aaagctaata aggacaggac agaagacaag caagatggta tgccaggaag | 240 |
| gtcatgggcc agcaaaaggg tctctgaatc tgtgaaggcc ttgctgttaa agggcaaagc | 300 |
| tcctgtggac ccagagtgta cagccaaggt ggggaaggct catgtgtatt gtgaaggaaa | 360 |
| tgatgtctat gatgtcatgc taaatcagac caatctccag ttcaacaaca acaagtacta | 420 |
| tctgattcag ctattagaag atgatgccca gaggaacttc agtgtttgga tgagatgggg | 480 |
| ccgagttggg aaaatgggac agcacagcct ggtggcttgt tcaggcaatc tcaacaaggc | 540 |
| caaggaaatc tttcagaaga aattccttga caaaacgaaa aacaattggg aagatcgaga | 600 |
| aaagtttgag aaggtgcctg aaaatatgaa tatgctacag atggactatg ccaccaatac | 660 |
| tcaggatgaa gaggaaacaa aaaagagga atctcttaaa tctcccttga gccagagtc | 720 |
| acagctagat cttcgggtac aggagttaat aaagttgatc tgtaatgttc aggccatgga | 780 |
| agaaatgatg atggaaatga agtataatac caagaaagcc ccacttggga agctgacagt | 840 |
| ggcacaaatc aaggcaggtt accagtctct taagaagatt gaggattgta ttcgggctgg | 900 |
| ccagcatgga cgagctctca tggaagcatg caatgaattc tacaccagga ttccgcatga | 960 |
| ctttggactc cgtactcctc cactaatccg gacacagaag gaactgtcag aaaaaataca | 1020 |
| attactagag gctttgggag acattgaaat tgctattaag ctggtgaaaa cagagctaca | 1080 |
| aagcccagaa cacccattgg accaacacta tagaaaccta cattgtgcct tgcgcccccct | 1140 |
| tgaccatgaa agttacgagt tcaaagtgat ttcccagtac ctacaatcta cccatgctcc | 1200 |
| cacacacagc gactatacca tgaccttgct ggatttgttt gaagtggaga aggatggtga | 1260 |
| gaaagaagcc ttcagagagg accttcataa caggatgctt ctatggcatg gttccaggat | 1320 |
| gagtaactgg gtgggaatct tgagccatgg gcttcgaatt gcccaccctg aagctcccat | 1380 |
| cacaggttac atgtttggga aaggaatcta ctttgctgac atgtcttcca agagtgccaa | 1440 |
| ttactgcttt gcctctcgcc taaagaatac aggactgctg ctcttatcag aggtagctct | 1500 |
| aggtcagtgt aatgaactac tagaggccaa tcctaaggcc gaaggattgc ttcaaggtaa | 1560 |
| acatagcacc aaggggctgg gcaagatggc tcccagttct gcccacttcg tcaccctgaa | 1620 |
| tgggagtaca gtgccattag gaccagcaag tgacacagga attctgaatc cagatggtta | 1680 |
| taccctcaac tacaatgaat atattgtata taaccccaac caggtccgta tgcggtacct | 1740 |

```
tttaaaggtt cagtttaatt tccttcagct gtggtgaatg ttgatcttaa ataaaccaga      1800
gatctgatct tcaagcaaga aaataagcag tgttgtactt gtgaattttg tgatatttta      1860
tgtaataaaa actgtacagg tctaaaaaaa aaaaaaaaaa aaaaaaaaaa                 1910

<210> SEQ ID NO 6
<211> LENGTH: 2263
<212> TYPE: DNA
<213> ORGANISM: Homo sapiens

<400> SEQUENCE: 6
tgggactggt cgcctgactc ggcctgcccc agcctctgct tcaccccact ggtggccaaa        60
tagccgatgt ctaatccccc acacaagctc atccccggcc tctgggattg ttgggaattc       120
tctccctaat tcacgcctga ggctcatgga gagttgctag acctgggact gccctgggag       180
gcgcacacaa ccaggccggg tggcagccag gacctctccc atgtccctgc ttttcttggc       240
catggctcca aagccgaagc cctgggtaca gactgagggc cctgagaaga agaagggccg       300
gcaggcagga agggaggagg accccttccg ctccaccgct gaggccctca aggccatacc       360
cgcagagaag cgcataatcc gcgtggatcc aacatgtcca ctcagcagca accccgggac       420
ccaggtgtat gaggactaca actgcaccct gaaccagacc aacatcgaga caacaacaa       480 caagttctac atcatccagc tgctccaaga cagcaaccgc ttcttcacct gctggaaccg       540
ctggggccgt gtgggagagg tcggccagtc aaagatcaac cacttcacaa ggctagaaga       600
tgcaaagaag gactttgaga agaaatttcg ggaaaagacc aagaacaact gggcagagcg       660
ggaccacttt gtgtctcacc cgggcaagta cacacttatc gaagtacagg cagaggatga       720
ggcccaggaa gctgtggtga aggtggacag aggcccagtg aggactgtga ctaagcgggt       780
gcagccctgc tccctggacc cagccacgca gaagctcatc actaacatct tcagcaagga       840
gatgttcaag aacaccatgg ccctcatgga cctggatgtg aagaagatgc cctgggaaa       900 gctgagcaag caacagattg cacggggttt cgaggcttg gaggcgctgg aggaggccct       960
gaaaggcccc acggatggtg gccaaagcct ggaggagctg tcctcacact tttacaccgt      1020
catcccgcac aacttcggcc acagccagcc ccgcccatc aattcccctg agcttctgca      1080
ggccaagaag gacatgctgc tggtgctggc ggacatcgag ctggcccagg ccctgcaggc      1140
agtctctgag caggagaaga cggtggagga ggtgccacac cccctggacc gagactacca      1200
gcttctcaag tgccagctgc agctgctaga ctctggagca cctgagtaca aggtgataca      1260
gacctactta gaacagactg gcagcaacca caggtgccct acacttcaac acatctggaa      1320
agtaaaccaa gaaggggagg aagacagatt ccaggcccac tccaaactgg gtaatcggaa      1380
gctgctgtgg catggcacca acatggccgt ggtggccgcc atcctcacta gtgggctccg      1440
catcatgcca cattctggtg ggcgtgttgg caagggcatc tactttgcct cagagaacag      1500
caagtcagct ggatatgtta ttggcatgaa gtgtggggcc caccatgtcg gctacatgtt      1560
cctgggtgag gtggccctgg gcagagagca ccatatcaac acggacaacc ccagcttgaa      1620
gagcccacct cctggcttcg acagtgtcat tgcccgaggc cacaccgagc ctgatccgac      1680
ccaggacact gagttggagc tggatggcca gcaagtggtg gtgccccagg ccagcctgt      1740 gccctgccca gagttcagca gctccacatt ctcccagagc gagtacctca tctaccagga      1800
gagccagtgt cgcctgcgct acctgctgga ggtccacctc tgagtgcccg ccctgtcccc      1860
cggggtcctg caaggctgga ctgtgatctt caatcatcct gcccatctct ggtacccta      1920 tatcactcct ttttttcaag aatacaatac gttgttgtta actatagtca ccatgctgta      1980
```

| | |
|---|---|
| caagatccct gaacttatgc ctcctaactg aaattttgta ttctttgaca catctgccca | 2040 |
| gtccctctcc tcccagccca tggtaaccag catttgactc tttacttgta taagggcagc | 2100 |
| ttttataggt tccacatgta agtgagatca tgcagtgttt gtctttctgt gcctggctta | 2160 |
| tttcactcag cataatgtgc accgggttca cccatgtttt cataaatgac aagatttcct | 2220 |
| cctttaaaaa aaaaaaaaaa aaaaaaaaaa aaaaaaaaaa aaa | 2263 |

<210> SEQ ID NO 7
<211> LENGTH: 4491
<212> TYPE: DNA
<213> ORGANISM: Homo sapiens

<400> SEQUENCE: 7

| | |
|---|---|
| cgaagatggc ggcgtcgcgt cgctctcagc atcatcacca ccatcatcaa caacagctcc | 60 |
| agcccgcccc aggggcttca gcgccgccgc cgccacctcc tccccactc agccctggcc | 120 |
| tggccccggg gaccacccca gcctctccca cggccagcgg cctggccccc ttcgcctccc | 180 |
| cgcggcacgg cctagcgctg ccggaggggg atggcagtcg ggatccgccc gacaggcccc | 240 |
| gatccccgga cccggttgac ggtaccagct gttgcagtac caccagcaca atctgtaccg | 300 |
| tcgccgccgc tcccgtggtc ccagcggttt ctacttcatc tgccgctggg gtcgctccca | 360 |
| acccagccgg cagtggcagt aacaattcac cgtcgtcctc ttcttcccg acttcttcct | 420 |
| catcttcctc tccatcctcc cctggatcga gcttggcgga gagccccgag gcggccggag | 480 |
| ttagcagcac agcaccactg gggcctgggg cagcaggacc tgggacaggg gtcccagcag | 540 |
| tgagcggggc cctacgggaa ctgctggagg cctgtcgcaa tggggacgtg tcccgggtaa | 600 |
| agaggctggt ggacgcggca aacgtaaatg caaaggacat ggccggccgg aagtcttctc | 660 |
| ccctgcactt cgctgcaggt tttggaagga aggatgttgt agaacactta ctacagatgg | 720 |
| gtgctaatgt ccacgctcgt gatgatggag gtctcatccc gcttcataat gcctgttctt | 780 |
| ttggccatgc tgaggttgtg agtctgttat tgtgccaagg agctgatcca aatgccaggg | 840 |
| ataactggaa ctatacacct ctgcatgaag ctgctattaa agggaagatc gatgtgtgca | 900 |
| ttgtgctgct gcagcacgga gctgacccaa acattcggaa cactgatggg aaatcagccc | 960 |
| tggacctggc agatccttca gcaaaagctg tccttacagg tgaatacaag aaagacgaac | 1020 |
| tcctagaagc tgctaggagt ggtaatgaag aaaaactaat ggctttactg actcctctaa | 1080 |
| atgtgaattg ccatgcaagt gatgggcgaa agtcgactcc tttacatcta gcagcgggct | 1140 |
| acaacagagt tcgaatagtt cagcttcttc ttcagcatgg tgctgatgtt catgcaaaag | 1200 |
| acaaaggtgg acttgtgcct cttcataatg catgttcata tggacattat gaagtcacag | 1260 |
| aactgctact aaagcatgga gcttgtgtta atgccatgga tctctggcag tttactccac | 1320 |
| tgcacgaggc tgcttccaag aaccgtgtag aagtctgctc tttgttactt agccatggcg | 1380 |
| ctgatcctac gttagtcaac tgccatggca aaagtgctgt ggatatggct ccaactccgg | 1440 |
| agcttaggga gagattgact tatgaattta aggtcattc tttactacaa gcagccagag | 1500 |
| aagcagactt agctaaagtt aaaaaaacac tcgctctgga aatcattaat ttcaaacaac | 1560 |
| cgcagtctca tgaaacagca ctgcactgtg ctgtggcctc tctgcatccc aaacgtaaac | 1620 |
| aagtgacaga attgttactt agaaaaggag caaatgttaa tgaaaaaaat aaagatttca | 1680 |
| tgactccccct gcatgttgca gccgaaagag cccataatga tgtcatggaa gttctgcata | 1740 |
| agcatggcgc caagatgaat gcactggaca cccttggtca gactgctttg catagagccg | 1800 |

-continued

```
ccctagcagg ccacctgcag acctgccgcc tcctgctgag ttacggctct gacccctcca    1860
tcatctcctt acaaggcttc acagcagcac agatgggcaa tgaagcagtg cagcagattc    1920
tgagtgtgag ttacggctct gacccctcca tcatctcctt acaaggcttc acagcagcac    1980
agatgggcaa tgaagcagtg cagcagattc tgagtggtca ttcgtagata gtgatcattc    2040
tacttcagcc ttaatggtga tcttgagacg ggaagattta gaaggaaatc tatccagcat    2100
gtcttcactg tcaacatgaa gagtacacct atacgtactt ctgatgttga ttatcgactc    2160
ttagaggcat ctaaagctgg agacttggaa actgtgaagc aactttgcag ctctcaaaat    2220
gtgaattgta gagacttaga gggccggcat tccacgccct tacacttcgc agcaggctac    2280
aacagagtac acctatacgt acttctgatg ttgattatcg actcttagag gcatctaaag    2340
ctggagactt ggaaactgtg aagcaacttt gcagctctca aaatgtgaat tgtagagact    2400
tagagggccg gcattccacg cccttacact tcgcagcagg ctacaaccgc gtgtctgttg    2460
tagagtacct gctacaccac ggtgccgatg tccatgccaa agacaagggt ggcttggtgc    2520
cccttcataa tgcctgttca tatggacact atgaggtggc tgagcttta gtaaggcatg    2580
gggcttctgt caatgtggcg gacttatgga aatttacccc tctccatgaa gcagcagcta    2640
aaggaaagta tgaaatctgc aagctccttt taaaacatgg agcagatcca actaaaaaga    2700
acagagatgg aaatacacct ttggatttgg taaggaagg agacacagat attcaggact    2760
tactgaaagg ggatgctgct tgttggatg ctgccaagaa gggctgcctg caagagtgc    2820
agaagctctg taccccagag aatatcaact gcagagacac ccagggcaga aattcaaccc    2880
ctctgcacct ggcagcaggc tataataacc tggaagtagc tgaatatctt ctagagcatg    2940
gagctgatgt taatgcccag acaaggggtg gtttaattcc tcttcataat gcggcatctt    3000
atgggcatgt tgacatagcg gctttattga taaaatacaa cacgtgtgta aatgcaacag    3060
ataagtgggc gtttactccc ctccatgaag cagcccagaa aggaaggacg cagctgtgcg    3120
ccctcctcct agcgcatggt gcagaccccca ccatgaagaa ccaggaaggc cagacgcctc    3180
tggatctggc aacagctgac gatatcagag ctttgctgat agatgccatg ccccagagg    3240
ccttacctac ctgtttttaaa cctcaggcta ctgtagtgag tgcctctctg atctcaccag    3300
catccacccc ctcctgcctc tcggctgcca gcagcataga caacctcact ggcccttag    3360
cagagttggc cgtaggagga gcctccaatg caggggatgg cgccgcggga acagaaagga    3420
aggaaggaga agttgctggt cttgacatga atatcagcca atttctaaaa agccttggcc    3480
ttgaacaccct tcgggatatc tttgaaacag aacagattac actagatgtg ttggctgata    3540
tgggtcatga agagttgaaa gaaataggca tcaatgcata tgggcaccgc cacaaattaa    3600
tcaaaggagt agaaagactc ttaggtggac aacaaggcac caatccttat ttgactttc    3660
actgtgttaa tcagggaacg attttgctgg atcttgctcc agaagataaa gaatatcagt    3720
cagtggaaga agagatgcaa agtactattc gagaacacag agatggtggt aatgctggcg    3780
gcatcttcaa cagatacaat gtcattcgaa ttcaaaaagt tgtcaacaag aagttgaggg    3840
agcggttctg ccaccgacag aaggaagtgt ctgaggagaa tcacaaccat cacaatgagc    3900
gcatgttgtt tcatggttct cctttcatta atgccattat tcataaaggg tttgatgagc    3960
gacatgcata cataggagga atgtttgggg ccgggattta ttttgctgaa aactcctcaa    4020
aaagcaacca atatgtttat ggaattggag gaggaacagg ctgccctaca cacaaggaca    4080
ggtcatgcta tatatgtcac agacaaatgc tcttctgtag agtgaccctt gggaaatcct    4140
ttctgcagtt tagcaccatg aaaatggccc acgcgcctcc agggcaccac tcagtcattg    4200
```

-continued

| | |
|---|---|
| gtagaccgag cgtcaatggg ctggcatatg ctgaatatgt catctacaga ggagaacagg | 4260 |
| catacccaga gtatcttatc acttaccaga tcatgaagcc agaagcccct tcccagaccg | 4320 |
| caacagccgc agagcagaag acctagtgaa tgcctgctgg tgaaggccag atcagatttc | 4380 |
| aacctgggac tggattacag aggattgttt ctaataacaa catcaatatt ctagaagtcc | 4440 |
| ctgacagcct agaaataagc tgtttgtctt ctataaagca ttgctatagt g | 4491 |

<210> SEQ ID NO 8
<211> LENGTH: 6189
<212> TYPE: DNA
<213> ORGANISM: Homo sapiens

<400> SEQUENCE: 8

| | |
|---|---|
| cgcgccgcct cgctagccga aacctgccca gccggtgccc ggccactgcg cacgcgcggg | 60 |
| acgacgtcac gtgcgctccc ggggctggac ggagctggca ggaggggcct tgccagcttc | 120 |
| cgccgccgcg tcgtttcagg acccggacgg cggattcgcg ctgcctccgc cgccgcgggg | 180 |
| cagccggggg gcagggagcc cagcgagggg cgcgcgtggg cgcggccatg ggactgcgcc | 240 |
| ggatccggtg acagcaggga gccaagcggc ccgggccctg agcgcgtctt ctccgggggg | 300 |
| cctcgccctc ctgctcgcgg ggccggggct cctgctccgg ttgctggcgc tgttgctggc | 360 |
| tgtggcggcg gccaggatca tgtcgggtcg ccgctgcgcc ggcgggggag cggcctgcgc | 420 |
| gagcgccgcg gccgaggccg tggagccggc cgcccgagag ctgttcgagg cgtgccgcaa | 480 |
| cggggacgtg gaacgagtca agaggctggt gacgcctgag aaggtgaaca gccgcgacac | 540 |
| ggcgggcagg aaatccaccc cgctgcactt cgccgcaggt tttgggcgga agacgtagt | 600 |
| tgaatatttg cttcagaatg gtgcaaatgt ccaagcacgt gatgatgggg gccttattcc | 660 |
| tcttcataat gcatgctctt ttggtcatgc tgaagtagtc aatctccttt tgcgacatgg | 720 |
| tgcagacccc aatgctcgag ataattggaa ttatactcct ctccatgaag ctgcaattaa | 780 |
| aggaaagatt gatgtttgca ttgtgctgtt acagcatgga gctgagccaa ccatccgaaa | 840 |
| tacagatgga aggacagcat tggatttagc agatccatct gccaaagcag tgcttactgg | 900 |
| tgaatataag aaagatgaac tcttagaaag tgccaggagt ggcaatgaag aaaaaatgat | 960 |
| ggctctactc acaccattaa atgtcaactg ccacgcaagt gatggcagaa agtcaactcc | 1020 |
| attacatttg gcagcaggat ataacagagt aaagattgta cagctgttac tgcaacatgg | 1080 |
| agctgatgtc catgctaaag ataaaggtga tctggtacca ttacacaatg cctgttctta | 1140 |
| tggtcattat gaagtaactg aacttttggt caagcatggt gcctgtgtaa atgcaatgga | 1200 |
| cttgtggcaa ttcactcctc ttcatgaggc agcttctaag aacaggggttg aagtatgttc | 1260 |
| tcttctctta agttatggtg cagacccaac actgctcaat tgtcacaata aaagtgctat | 1320 |
| agacttggct cccacaccac agttaaaaga aagattagca tatgaattta aaggccactc | 1380 |
| gttgctgcaa gctgcacgag aagctgatgt tactcgaatc aaaaaacatc tctctctgga | 1440 |
| aatggtgaat tcaagcatcc tcaaacacat gaaacagcat tgcattgtg ctgctgcatc | 1500 |
| tccatatccc aaaagaaagc aaatatgtga actgttgcta agaaaggag caaacatcaa | 1560 |
| tgaaaagact aaagaattct tgactcctct gcacgtggca tctgagaaag ctcataatga | 1620 |
| tgttgttgaa gtagtggtga acatgaagc aaaggttaat gctctggata atcttggtca | 1680 |
| gacttctcta cacagagctg catattgtgg tcatctacaa acctgccgcc tactcctgag | 1740 |
| ctatgggtgt gatcctaaca ttatatccct tcagggcttt actgctttac agatgggaaa | 1800 |

```
tgaaaatgta cagcaactcc tccaagaggg tatctcatta ggtaattcag aggcagacag    1860
acaattgctg gaagctgcaa aggctggaga tgtcgaaact gtaaaaaaac tgtgtactgt    1920
tcagagtgtc aactgcagag acattgaagg gcgtcagtct acaccacttc attttgcagc    1980
tgggtataac agagtgtccg tggtggaata tctgctacag catggagctg atgtgcatgc    2040
taaagataaa ggaggccttg tacctttgca caatgcatgt tcttatggac attatgaagt    2100
tgcagaactt cttgttaaac atggagcagt agttaatgta gctgatttat ggaaatttac    2160
acctttacat gaagcagcag caaaaggaaa atatgaaatt tgcaaacttc tgctccagca    2220
tggtgcagac cctacaaaaa aaaacaggga tggaaatact cctttggatc ttgttaaaga    2280
tggagataca gatattcaag atctgcttag gggagatgca gctttgctag atgctgccaa    2340
gaagggttgt ttagccagag tgaagaagtt gtcttctcct gataatgtaa attgccgcga    2400
tacccaaggc agacattcaa cacctttaca tttagcagct ggttataata atttagaagt    2460
tgcagagtat ttgttacaac acggagctga tgtgaatgcc caagacaaag gaggacttat    2520
tcctttacat aatgcagcat cttacgggca tgtagatgta gcagctctac taataaagta    2580
taatgcatgt gtcaatgcca cggacaaatg gctttcaca cctttgcacg aagcagccca    2640
aaagggacga acacagcttt gtgctttgtt gctagcccat ggagctgacc cgactcttaa    2700
aaatcaggaa ggacaaacac ctttagattt agtttcagca gatgatgtca gcgctcttct    2760
gacagcagcc atgcccccat ctgctctgcc ctcttgttac aagcctcaag tgctcaatgg    2820
tgtgagaagc ccaggagcca ctgcagatgc tctctcttca ggtccatcta gcccatcaag    2880
cctttctgca gccagcagtc ttgacaactt atctggagt tttcagaac tgtcttcagt    2940 agttagttca agtggaacag agggtgcttc cagtttggag aaaaaggagg ttccaggagt    3000
agattttagc ataactcaat tcgtaaggaa tcttggactt gagcacctaa tggatatatt    3060
tgagagagaa cagatcactt tggatgtatt agttgagatg gggcacaagg agctgaagga    3120
gattggaatc aatgcttatg gacataggca caaactaatt aaaggagtcg agagactat    3180 ctccggacaa caaggtctta acccatattt aactttgaac acctctggta gtggaacaat    3240
tcttatagat ctgtctcctg atgataaga gtttcagtct gtggaggaag agatgcaaag    3300
tacagttcga gagcacagag atggaggtca tgcaggtgga atcttcaaca gatacaatat    3360
tctcaagatt cagaaggttt gtaacaagaa actatgggaa agatacactc accgagaaaa    3420
agaagtttct gaagaaaacc acaaccatgc caatgaacga atgctatttc atgggtctcc    3480
ttttgtgaat gcaattatcc acaaaggctt tgatgaaagg catgcgtaca taggtggtat    3540
gtttggagct ggcatttatt ttgctgaaaa ctcttccaaa agcaatcaat atgtatatgg    3600
aattggagga ggtactgggt gtccagttca caagacagatc ttgttaca tttgccacag    3660 gcagctgctc ttttgccggg taaccttggg aaagtctttc ctgcagttca gtgcaatgaa    3720
aatggcacat tctcctccag gtcatcactc agtcactggt aggcccagtg taaatggcct    3780
agcattagct gaatatgtta tttacagagg agaacaggct tatcctgagt atttaattac    3840
ttaccagatt atgaggcctg aaggtatggt cgatggataa atagttattt taagaaacta    3900
attccactga acctaaaatc atcaaagcag cagtggcctc tacgttttac tcctttgctg    3960
aaaaaaaatc atcttgccca caggcctgtg gcaaaggat aaaaatgtga acgaagttta    4020
acattctgac ttgataaagc tttaataatg tacagtgttt tctaaatatt tcctgttttt    4080
tcagcacttt aacagatgcc attccaggtt aaactgggt gtctgtacta aattataaac    4140
agagttaact tgaaccttt atatgttatg cattgattct aacaaactgt aatgccctca    4200
```

```
acagaactaa ttttactaat acaatactgt gttctttaaa acacagcatt tacactgaat    4260
acaatttcat ttgtaaaact gtaaataaga gcttttgtac tagcccagta tttatttaca    4320
ttgctttgta atataaatct gttttagaac tgcagcggtt tacaaaattt tttcatatgt    4380
attgttcatc tatacttcat cttacatcgt catgattgag tgatctttac atttgattcc    4440
agaggctatg ttcagttgtt agttgggaaa gattgagtta tcagatttaa tttgccgatg    4500
ggagccttta tctgtcatta gaaatctttc tcatttaaga acttatgaat atgctgaaga    4560
tttaatttgt gataccttg tatgtatgag acacattcca aagagctcta actatgatag     4620
gtcctgatta ctaaagaagc ttctttactg gcctcaattt ctagctttca tgttggaaaa    4680
ttttctgcag tccttctgtg aaaattagag caaagtgctc ctgttttta gagaaactaa     4740 atcttgctgt tgaacaatta ttgtgttctt ttcatggaac ataagtagga tgttaacatt    4800
tccagggtgg aagggtaat cctaaatcat ttcccaatct attctaatta ccttaaatct     4860 aaagggaaa aaaaaatca caaacaggac tgggtagttt tttatcctaa gtatattttt      4920
tcctgttctt tttacttggt tttattgctg tatttatagc caatctatac atcatgggta    4980
aacttaaccc agaactataa aatgtagttg tttcagtccc cttcaggcct cctgaatggg    5040
caagtgcagt gaaacaggtg cttcctgctc ctgggttttc tctccatgat gttatgccca    5100
attggaaata tgctgtcagt ttgtgcacca tatggtgacc acgcctgtgc tcagtttggc    5160
agctatagaa ggaaatgctg tcccataaaa tgccatccct atttctaata taacactctt    5220
ttccaggaag catgcttaag catcttgtta cagagacata catccattat ggcttggcaa    5280
tctcttttat ttgttgactc tagctccctt caaagtcgag gaaagatctt tactcactta    5340
atgaggacat tccccatcac tgtctgtacc agttccacctt tattttacgt tttattcagt   5400
ctgtaaatta actggcccctt tgcagtaact tgtacataaa gtgctagaaa atcatgttcc    5460
ttgtcctgag taagagttaa tcagagtaag tgcattctg gagttgtttc tgtgatgtaa     5520
attatgatca ttattaaga agtcaaatcc tgatcttgaa gtgcttttta tacagctctc     5580
taataattac aaatatccga aagtcatttc ttggaacaca agtggagtat gccaaatttt    5640
atatgaattt ttcagattat ctaagcttcc aggttttata attagaagat aatgagagaa    5700
ttaatggggt ttatatttac attatctctc aactatgtag cccatattac tcaccctatg    5760
agtgaatctg gaattgcttt tcatgtgaaa tcattgtggt ctatgagttt acaatactgc    5820
aaactgtgtt atttatcta aaccattgct taatgagtgt gtttttccat gaatgaatat     5880
accgtggttc atatgttagc atggcagcat tttcagatag ctttttgttt gttgggaagt    5940 tgggttttg ggggagggg gagtattagt acgttgcatg aatagccta ctttataatg       6000 atgggaatgc ttttctttt gttttgggat tttttttttt gaagtgaaat ttaactttt      6060 gtgccagtag tactattata cccatcttca gtgtcttact tgtactgtat caaattccat    6120
accctcattt aattccttaat aaaactgttc acttgtaaaa aaaaaaaaa aaaaaaaaa     6180 aaaaaaaa                                                              6189
```

<210> SEQ ID NO 9
<211> LENGTH: 5490
<212> TYPE: DNA
<213> ORGANISM: Homo sapiens

<400> SEQUENCE: 9

```
cgcccgccca gccccggggg cagggaaagc ctaaattacg gaattaccgc gagcaaggag    60
```

```
cgcggaatcg gggagcgtcc ggagctagct ggatcctcta ggcaggatgg tgatgggaat    120
ctttgcaaat tgtatcttct gtttgaaagt gaagtactta cctcagcagc agaagaaaaa    180
gctacaaact gacattaagg aaaatggcgg aaagttttcc ttttcgttaa atcctcagtg    240
cacacatata atcttagata atgctgatgt tctgagtcag taccaactga attctatcca    300
aaagaaccac gttcatattg caaacccaga ttttatatgg aaatctatca gagaaaagag    360
actcttggat gtaaagaatt atgatcctta taagccctg gacatcacac cacctcctga     420
tcagaaggcg agcagttctg aagtgaaaac agaaggtcta tgcccggaca gtgccacaga    480
ggaggaagac actgtggaac tcactgagtt tggtatgcag aatgttgaaa ttcctcatct    540
tcctcaagat tttgaagttg caaaatataa caccttggag aaagtgggaa tggagggagg    600
ccaggaagct gtggtggtgg agcttcagtg ttcgcgggac tccagggact gtccttcct     660 gatatcctca cacttcctcc tggatgatgg catggagact agaagacagt ttgctataaa    720
gaaaacctct gaagatgcaa gtgaatactt tgaaaattac attgaagaac tgaagaaaca    780
aggatttcta ctaagagaac atttcacacc tgaagcaacc caattagcat ctgaacaatt    840
gcaagcattg cttttggagg aagtcatgaa ttcaagcact ctgagccaag aggtgagcga    900
tttagtagag atgatttggg cagaggccct gggccacctg aacacatgc ttctcaagcc     960 agtgaacagg attagcctca acgatgtgag caaggcagag gggattctcc ttctagtaaa   1020
ggcagcactg aaaaatggag aaacagcaga gcaattgcaa aagatgatga cagagtttta   1080
cagactgata cctcacaaag gcacaatgcc caagaagtg aacctgggac tattggctaa    1140
gaaagcagac ctctgccagc taataagaga catggttaat gtctgtgaaa ctaatttgtc   1200
caaacccaac ccaccatccc tggccaaata ccgagctttg aggtgcaaaa ttgagcatgt   1260
tgaacagaat actgaagaat ttctcagggt tagaaaagag ttttgcaga atcatcacag    1320 taagagccca gtggatgtct tgcagatatt tagagttggc agagtgaatg aaaccacaga   1380 gttttttgagc aaacttggta atgtgaggcc cttgttgcat ggttctcctg tacaaaacat   1440
cgtgggaatc ttgtgtcgag ggttgctttt acccaaagta gtggaagatc gtggtgtgca   1500
aagaacagac gtcggaaacc ttggaagtgg gatttatttc agtgattcgc tcagtacaag   1560
tatcaagtac tcacacccgg gagagacaga tggcaccaga ctcctgctca tttgtgacgt   1620
agccctcgga aagtgtatgg acttacatga aaggactttt cccttaactg aagcaccacc   1680
aggctacgac agtgtgcatg gagtttcaca acagcctct gtcaccacag actttgagga    1740
tgatgaattt gttgtctata aaccaatca ggttaaaatg aaatatatta ttaaattttc    1800
catgcctgga gatcagataa aggactttca tcctagtgat catactgaat agaggaata    1860 cagacctgag ttttcaaatt tttcaaaggt tgaagattac cagttaccag atgccaaaac   1920
ttccagcagc accaaggccg gcctccagga tgcctctggg aacttggttc ctctggagga   1980
tgtccacatc aaagggagaa tcatagacac tgtagcccag gtcattgttt ttcagacata   2040
cacaaataaa agtcacgtgc ccattgaggc aaaatatatc tttccttggg atgacaaggc   2100
cgctgtgtgt ggcttcgaag ccttcatcaa tgggaagcac atagttggag agattaaaga   2160
gaaggaagaa gcccagcaag agtacctaga agccgtgacc cagggccatg cgcttacct    2220 gatgagtcag gatgctccgg acgttttac tgtaagtgtt ggaaacttac cccctaaggc    2280
taaggttctt ataaaaatta cctacatcac agaactcagc atcctgggca ctgttggtgt   2340 cttttttcatg cccgccaccg tagcaccctg gcaacaggaa aaggctttga atgaaaacct   2400
tcaggataca gtagagaaga tttgtataaa agaaatagga acaaagcaaa gcttctcttt   2460
```

```
gactatgtct attgagatgc cgtatgtgat tgaattcatt ttcagtgata cacatgaact     2520
gaaacaaaag cgcacagact gcaaagctgt cattagcacc atggaaggca gctccttaga     2580
cagcagtgga ttttctctcc acatcggttt gtctgctgcc tatctcccaa gaatgtgggt     2640
tgaaaaacat ccagaaaaag aaagcgaggc ttgcatgctt gtctttcaac ccgatctcga     2700
tgtcgacctc cctgacctag ccagtgagag cgaagtgatt atttgtcttg actgctccag     2760
ttccatggag ggtgtgacat tcttgcaagc caagcaaatc accttgcatg cgctgtcctt     2820
ggtgggtgag aagcagaaag taaatattat ccagttcggc acaggttaca aggagctatt     2880
ttcgtatcct aagcatatca caagcaatac cacggcagca gagttcatca tgtctgccac     2940
acctaccatg gggaacacag acttctggaa aacactccga tatcttagct tattgtaccc     3000
tgctcgaggg tcacggaaca tcctcctggt gtctgatggg cacctccagg atgagagcct     3060
gacattacag ctcgtgaaga ggagccgccc gcacaccagg ttattcgcct gcggtatcgg     3120
ttctacagca atcgtcacg tcttaaggat tttgtcccag tgtggtgccg gagtatttga     3180
atattttaat gcaaaatcca agcatagttg gagaaaacag atagaagacc aaatgaccag     3240
gctatgttct ccgagttgcc actctgtctc cgtcaaatgg cagcaactca atccagatgc     3300
gcccgaggcc ctgcaggccc cagcccaggt gccatccttg tttcgcaatg atcgactcct     3360
tgtctatgga ttcattcctc actgcacaca agcaactctg tgtgcactaa ttcaagagaa     3420
agaattttgt acaatggtgt cgactactga gcttcagaag acaactggaa ctatgatcca     3480
caagctggca gcccgagctc taatcagaga ttatgaagat ggcattcttc acgaaaatga     3540
aaccagtcat gagatgaaaa acaaaccctt gaaatctctg attattaaac tcagtaaaga     3600
aaactctctc ataacacaat ttacaagctt tgtggcagtt gagaaaaggg atgagaatga     3660
gtcgcctttt cctgatattc caaaagtttc tgaacttatt gccaagaag atgtagactt      3720 cctgccctac atgagctggc aggggagcc ccaagaagcc gtcaggaacc agtctctttt      3780
agcatcctct gagtggccag aattacgttt atccaaacga aaacatagga aaattccatt     3840
ttccaaaaga aaatggaat tatctcagcc agaagtttct gaagattttg aagaggatgg      3900
cttaggtgta ctaccagctt tcacatcaaa tttggaacgt ggaggtgtgg aaaagctatt     3960
ggatttaagt tggacagagt catgtaaacc aacagcaact gaaccactat ttaagaaagt     4020
cagtccatgg gaaacatcta cttctagctt ttttcctatt ttggctccgg ccgttggttc     4080
ctatcttacc ccgactaccc gcgctcacag tcctgcttcc ttgtcttttg cctcatatcg     4140
tcaggtagct agtttcggtt cagctgctcc tcccagacag tttgatgcat ctcaattcag     4200
ccaaggccct gtgcctggca cttgtgctga ctggatccca cagtcggcgt cttgtcccac     4260
aggacctccc cagaacccac cttctgcacc ctattgtggc attgtttttt cagggagctc     4320
attaagctct gcacagtctg ctccactgca acatcctgga ggctttacta ccaggccttc     4380
tgctggcacc ttccctgagc tggattctcc ccagcttcat ttctctcttc ctacagaccc     4440
tgatcccatc agaggttttg ggtcttatca tccctctgct tactctcctt ttcattttca     4500
accttccgca gcctctttga ctgccaacct taggctgcca atggcctctg ctttacctga     4560 ggctcttttgc agtcagtccc ggactacccc agtagatctc tgtcttctag aagaatcagt     4620
aggcagtctc gaaggaagtc gatgtcctgt ctttgctttt caaagttctg acacagaaag     4680
tgatgagcta tcgaagtac ttcaagacag ctgctttta caaataaagt gtgatacaaa       4740
agatgacagt atcccgtgct ttctggaatt aaaagaagag gatgaaatag tgtgcacaca     4800
```

```
                                              -continued
acactggcag gatgctgtgc cttggacaga actcctcagt ctacagacag aggatggctt      4860
ctggaaactt acaccagaac tgggacttat attaaatctt aatacaaatg gtttgcacag      4920
ctttcttaaa caaaaaggca ttcaatctct aggtgtaaaa ggaagagaat gtctcctgga      4980
cctaattgcc acaatgctgg tactacagtt tattcgcacc aggttggaaa aagagggaat      5040
agtgttcaaa tcactgatga aaatggatga cccttctatt tccaggaata ttccctgggc      5100
ttttgaggca ataaagcaag caagtgaatg ggtaagaaga actgaaggac agtacccatc      5160
tatctgccca cggcttgaac tggggaacga ctgggactct gccaccaagc agttgctggg      5220
actccagccc ataagcactg tgtcccctct tcatagagtc ctccattaca gtcaaggcta      5280
agtcaaatga aactgaattt taaacttttt gcatgcttct atgtagaaaa taatcaaatg      5340
ataatagata attataatga aacttcatta aggtttcatt cagtgtagca attactgtct      5400
ttaaaaatta agtggaagaa gaattacttt aatcaactaa caagcaataa taaaatgaaa      5460
cttaaaataa aaaaaaaaaa aaaaaaaaa                                        5490
```

USE OF RNAI INHIBITING PARP ACTIVITY FOR THE MANUFACTURE OF A MEDICAMENT FOR THE TREATMENT OF CANCER

This invention relates to the use of an agent that inhibits the activity of an enzyme which mediates the repair of DNA strand breaks in the treatment of certain forms of cancer in particular breast cancer.

Homologous recombination (HR) has been shown to play an important role in repair of damage occurring at DNA replication forks in mammalian cells (2). Thus, cells deficient in HR show retarded growth and exhibit higher level of genetic instability. It is believed that genetic instability due to loss of HR repair in human cancers significantly contributes to the development of cancer in these cells (1).

Post transcriptional modification of nuclear proteins by poly(ADP-ribosyl)ation (PARP) in response to DNA strand breaks plays an important role in DNA repair, regulation of apoptosis, and maintenance of genomic stability.

Poly(ADP-ribose)Polymerase (PARP-1) is an abundant nuclear protein in mammalian cells that catalyses the formation of poly(ADP-ribose) (PAR) polymers using $NAD^+$ as substrate. Upon DNA damage, PARP-1 binds rapidly to a DNA strand break (single strand or double strand) and catalyses the addition of negatively charged PAR chains to itself (automodification) and other proteins (see [3, 4] for reviews). The binding of PARP-1 to DNA strand breaks is believed to protect DNA lesions from further processing until PARP-1 is dissociated from the break by the accumulated negative charge resulting from PAR polymers (5,6).

Although PARP-1 has been implicated in several nuclear processes, such as modulation of chromatin structure, DNA replication, DNA repair and transcription, PARP-1 knockout mice develop normally (7). Cells isolated from these mice exhibit a hyper recombination phenotype and genetic instability in the form of increased levels of SCE, micronuclei and tetraploidy (8-10). Genetic instability may also occur in these PARP-1 knockout mice through telomere shortening, increased frequency of chromosome fusion and aneuploidy (11), although all of these results could not be repeated in another set of PARP-1 knock-out mice (12). In the former mice knockout, PARP-1 null mutation rescue impaired V(D)J recombination in SCID mice (13).

These results support the view suggested by Lindahl and coworkers that PARP-1 has a protective role against recombination (5). They proposed that binding of PARP-1 to DNA strand breaks prevents the recombination machinery from recognizing and processing DNA lesions or, alternatively, that the negative charges accumulated following poly ADP-ribosylation repel adjacent recombinogenic DNA sequences. Only the latter model is consistent with inhibition of PARP-1 itself and expression of a dominant negative mutant PARP-1, inducing SCE, gene amplification and homologous recombination (HR [14-18]).

Studies based on treating cells with PARP inhibitors or cells derived from PARP-1 or PARP-2 knockout mice indicate that the suppression of PARP-1 activity increases cell susceptibility to DNA damaging agents and inhibits strand break rejoining (3, 4, 8-11, 19, 20, 47).

Inhibitors of PARP-1 activity have been used in combination with traditional anti-cancer agents such as radio therapy and chemotherapy (21). The inhibitors were used in combination with methylating agents, topoisomerase poisons and ionising radiations and were found to enhance the effectiveness of these forms of treatment. Such treatments, however, are known to cause damage and death to non cancerous or "healthy" cells and are associated with unpleasant side effects.

There is therefore a need for a treatment for cancer that is both effective and selective in the killing of cancer cells and which does not need to be administered in combination with radio or chemotherapy treatments.

The present inventors have surprisingly found that cells deficient in homologous recombination (HR) are hypersensitive to PARP inhibitors as compared to wild type cells. This is surprising since PARP-1 knockout mice live normally thereby indicating that PARP-1 is not essential for life. Thus, it could not be expected that cells would be sensitive to PARP inhibition.

According to a first aspect of the invention there is provided the use of an agent that inhibits the activity of an enzyme that mediates the repair of DNA strand breaks in the manufacture of a medicament for the treatment of diseases that are caused by a genetic defect in a gene that mediates homologous recombination.

In a further aspect the invention provides a method of treatment of a disease or condition in a mammal, including human, which is caused by a genetic defect in a gene which mediates homologous recombination, which method comprises administering to the mammal a therapeutically effective amount of an agent which inhibits the activity of an enzyme which mediates repair of DNA strand breaks or other lesions present at replication forks.

In a preferred aspect said enzyme is PARP. In a further preferred aspect said agent is a PARP inhibitor or an RNAi molecule specific to PARP gene.

In a further preferred aspect, the use is in the treatment of cancer.

Preferably the medicament is a pharmaceutical composition consisting of the PARP inhibitor in combination with a pharmaceutically acceptable carrier or diluent.

The specific sensitivity of HR defective tumours to PARP-1 inhibition means that normally dividing cells in the patient will be unaffected by the treatment. Treatment of HR defective cancer cells using a PARP inhibitor also has the advantage that it does not need to be administered as a combination therapy along with conventional radio or chemotherapy treatments thereby avoiding the side effects associated with these conventional forms of treatment.

A genetic defect in a gene which mediates homologous recombination may be due to a mutation in, the absence of, or defective expression of, a gene encoding a protein involved in HR.

In a further aspect, the invention further provides the use of a PARP inhibitor in the manufacture of a medicament for inducing apoptosis in HR defective cells.

In another aspect the invention provides a method of inducing apoptosis in HR defective cells in a mammal which method comprises administering to the mammal a therapeutically effective amount of a PARP inhibitor.

By causing apoptosis in HR defective cells it should be possible to reduce or halt the growth of a tumour in the mammal.

Preferably, the HR defective cells are cancer cells.

Cancer cells defective in HR may partially or totally deficient in HR. Preferably the cancer cells are totally deficient in HR.

The term "cancer" or "tumour" includes lung, colon, pancreatic, gastric, ovarian, cervical, breast or prostate cancer. The cancer may also include skin, renal, liver, bladder or cerebral cancer. In a preferred aspect, the cancer is in a mammal, preferably human.

The cancer to be treated may be an inherited form of cancer wherein the patient to be treated has a familial predisposition to the cancer. Preferably, the cancer to be treated is gene-linked hereditary cancer. In a preferred embodiment of the invention the cancer is gene-linked hereditary breast cancer.

In a preferred aspect, the PARP inhibitor is useful in the treatment of cancer cells defective in the expression of a gene involved in HR. Genes with suggested function in HR include XRCC1, ADPRT (PARP-1), ADPRTL2 (PARP-2), CTPS, RPA, RPA1, RPA2, RPA3, XPD, ERCC1, XPF, MMS19, RAD51, RAD51B, RAD51C, RAD51D, DMC1, XRCC2, XRCC3, BRCA1, BRCA2, RAD52, RAD54, RAD50, MRE11, NBS1, WRN, BLM, Ku70, Ku80, ATM, ATR, chk1, chk2, FANCA, FANCB, FANCC, FANCD1, FANCD2, FANCE, FANCF, FANCG, RAD1, RAD9, FEN-1, Mus81. Eme1, DDS1, BARD (see (2, 3, 5, 22-28) for reviews).

A gene involved in HR may be a tumour suppressor gene. The invention thus provides for the treatment of cancer cells defective in the expression of a tumour suppressor gene. Preferably, the tumour suppressor gene is BRCA1 or BRCA2.

Breast cancer is the most common cancer disease among women in the Western world today. Certain families have strong predisposition for breast cancer, which is often owing to an inherited mutation in one allele of either BRCA1 or BRCA2. However, these patients still maintain one functional allele. Thus, these patients develop normally and have no phenotypic consequence from this mutation. However, in one cell, the functional allele might be lost, making this cell cancerous and at the same time deficient in homologous recombination (HR). This step is critical for the onset of a tumour (1).

The present inventors have surprisingly found that BRCA2 deficient cells are 100 times more sensitive to the cytotoxicity of the PARP inhibitor, NU1025, than wild type cells.

Thus in a preferred aspect, the invention provides the use of a PARP inhibitor in the manufacture of a medicament for the treatment of cancer cells defective in HR, e.g due to the loss of BRCA1 and/or BRCA2 expression.

The cancer cells to be treated may be partially or totally deficient in BRCA1 or BRCA2 expression. BRCA1 and BRCA2 mutations can be identified using multiplex PCR techniques, array techniques (29, 30) or using other screens known to the skilled person.

PARP inhibitors useful in the present invention may be selected from inhibitors of PARP-1, PARP-2, PARP-3, PARP-4, tankyrase 1 or tankyrase 2 (see 31 for a review). In a preferred embodiment, the PARP inhibitor useful in the present invention is an inhibitor of PARP-1 activity.

PARP inhibitors useful in the present invention include benzimidazole-carboxamides, quinazolin-4-[3H]-ones and isoquinoline derivatives (e.g. 2-(4-hydroxyphenyl)benzimidazole-4-carboxamide (NU1085), 8-hydroxy-2-methylquinazolin-4-[3H]one (NU1025); 6(5H)phenanthridinone; 3 aminobenzamide; benzimidazole-4-carboxamides (BZ1-6) and tricyclic lactam indoles (TI1-5) [32]. Further inhibitors of PARP may be identified either by design [33] or the novel FlashPlate assay [34].

The PARP inhibitor formulated as a pharmaceutical composition may be administered in any effective, convenient manner effective for targeting cancer cells including, for instance, administration by oral, intravenous, intramuscular, intradermal, intranasal, topical routes among others. Carriers or diluents useful in the pharmaceutical composition may include, but are not limited to saline, buffered saline, dextrose, water, glycerol, ethanol and combinations thereof.

In therapy or as a prophylactic, the active agent may be administered to an individual as an injectable composition, for example as a sterile aqueous dispersion. The inhibitor may be administered directly to a tumour or may be targeted to the tumour via systemic administration.

A therapeutically effective amount of the inhibitor is typically one which is sufficient to achieve the desired effect and may vary according to the nature and severity of the disease condition, and the potency of the inhibitor. It will be appreciated that different concentrations may be employed for prophylaxis than for treatment of an active disease.

For administration to mammals, and particularly humans, it is expected that the daily dosage level of the active agent will be up to 100 mg/kg, for example from 0.01 mg/kg to 50 mg/kg body weight, typically up to 0.1, 0.5, 1.0, 2.0 5.0, 10, 15, 20 or 30 mg/kg body weight. Ultimately, however, the amount of inhibitor administered and the frequency of administration will be at the discretion of a physician.

A therapeutic advantage of using PARP inhibitors to treat cancer cells is that only very low doses are needed to have a therapeutic effect in treating cancer thereby reducing systemic build up of the inhibitors and any associated toxic effects.

A preferred aspect of the invention provides an agent which is an inhibitory RNA (RNAi) molecule.

A technique to specifically ablate gene function is through the introduction of double stranded RNA, also referred to as inhibitory RNA (RNAi), into a cell which results in the destruction of mRNA complementary to the sequence included in the RNAi molecule. The RNAi molecule comprises two complementary strands of RNA (a sense strand and an antisense strand) annealed to each other to form a double stranded RNA molecule. The RNAi molecule is typically derived from exonic or coding sequence of the gene which is to be ablated.

Preferably said RNAi molecule is derived from the nucleic acid molecule comprising a nucleic acid sequence selected from the group consisting of:
  a) a nucleic acid sequence as represented by the sequence in FIG. 9, 10, 11, 12, 13 or 14 or fragment thereof;
  b) a nucleic acid sequence which hybridises to the nucleic acid sequences of FIG. 9, 10, 11, 12, 13 or 14 and encodes a gene for PARP;
  c) a nucleic acid sequence which comprise sequences which are degenerate as a result of the genetic code to the nucleic acid sequences defined in (a) and (b).

Recent studies suggest that RNAi molecules ranging from 100-1000 bp derived from coding sequence are effective inhibitors of gene expression. Surprisingly, only a few molecules of RNAi are required to block gene expression which implies the mechanism is catalytic. The site of action appears to be nuclear as little if any RNAi is detectable in the cytoplasm of cells indicating that RNAi exerts its effect during mRNA synthesis or processing.

More preferably said RNAi molecule according has a length of between 10 nucleotide bases (nb)-1000 nb. Even more preferably said RNAi molecule has a length of 10 nb; 20 nb; 30 nb; 40 nb; 50 nb; 60 nb; 70 nb; 80 nb; 90 nb; or 100 bp. Even more preferably still said RNAi molecule is 21 nb in length.

Even more preferably still the RNAi molecule comprises the nucleic acid sequence aaa agc cau ggu gga gua uga (PARP-1)

Even more preferably still the RNAi molecule consists of the nucleic acid sequence aag acc aau cuc ucc agu uca ac (PARP-2)

Even more preferably still the RNAi molecule consists of the nucleic acid sequence aag acc aac auc gag aac aac (PARP-3)

The RNAi molecule may comprise modified nucleotide bases.

Preferred features of each aspect of the invention are as for each of the other aspects *mutatis mutandis*.

The present invention will now be described by way of example only with reference to the accompanying figures, wherein:

FIG. 1 is a graph demonstrating that HR deficient cells are hypersensitive to the toxic effect caused by inhibition of PARP-1. Colony outgrowth of the Chinese hamster cell lines AA8 (wild-type), irs1SF (deficient in HR[4]), CXR3 (irs1SF complemented with XRCC3 [2]), V79 (wild-type), irs1 (deficient in HR[5]) or irs1X2.2 (irs1 complimented with XRCC2 [1]) upon exposure to 3-AB (A), ISQ (B) or NU1025 (C). The means (symbols) and standard deviation (bars) of at least three experiments are shown. Colony outgrowth assay was used;

Figure 4:
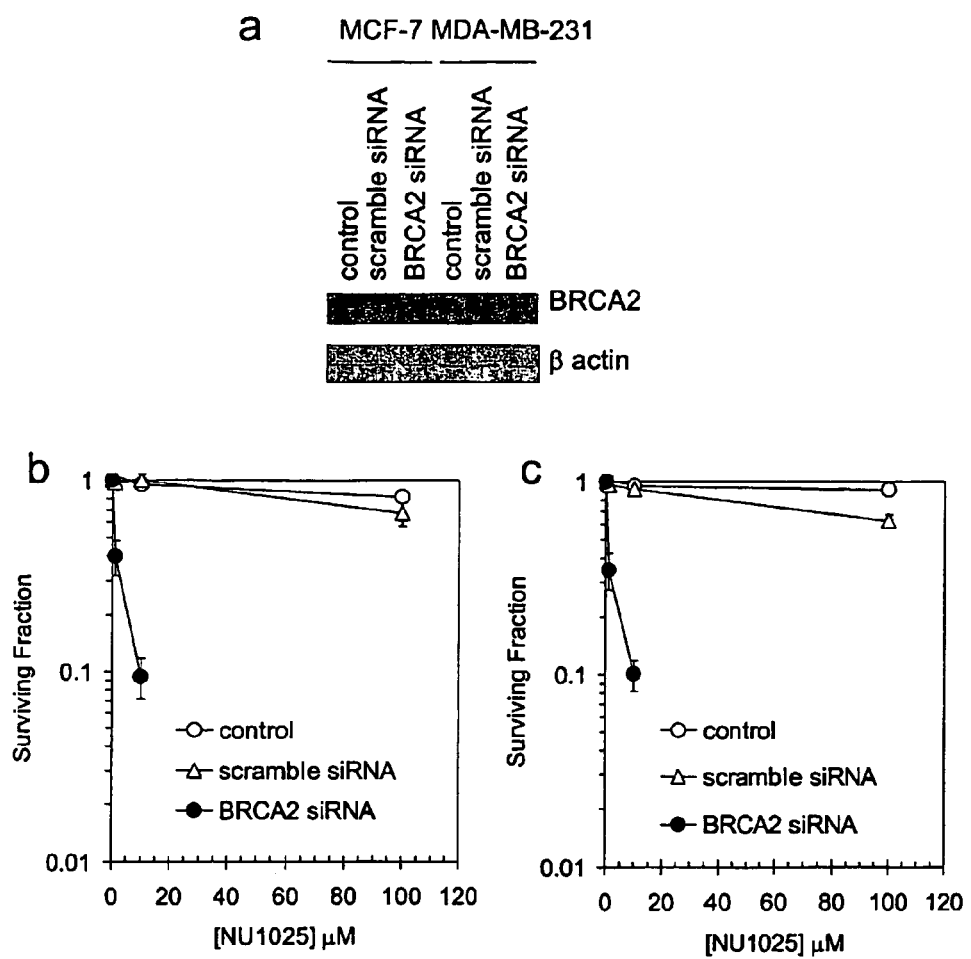

FIG. 4. (a) Western blot analysis of protein lysates isolated from MCF-7 ($p53^{wt}$) or MDA-MB-231 ($p53^{mut}$) breast cancer cells following 48 hours transfection with siRNA. (b) Colony outgrowth of siRNA-treated MCF-7 cells or (c) MDA-MB-231 cells following exposure to the PARP inhibitor NU1025. The means (symbols) and standard deviation (bars) of at least three experiments are shown.

FIG. 5. BRCA2 deficient cells fail to repair a recombination lesion formed at replication forks by inhibitors of PARP. (a) Visualization of double strand breaks (DSBs) in BRCA2 proficient or deficient cells following a 24-hour treatment with NU1025 (0.1 mM) by pulse-field gel electrophoresis. Hydroxyurea 2 mM was used as a positive control. (b) Visualisation of γH2Ax foci in untreated V-C8+B2 and V-C8 cells. Number of cells containing γH2Ax foci (c) or RAD51 foci (d) visualised in V-C8+B2 and V-C8 cells following a 24-hour treatment with NU1025 (10 μM). The means (symbols) and standard errors (bars) of three to nine experiments are shown. (e) A suggested model for cell death induced in BRCA2 deficient cells.

Figure 6:
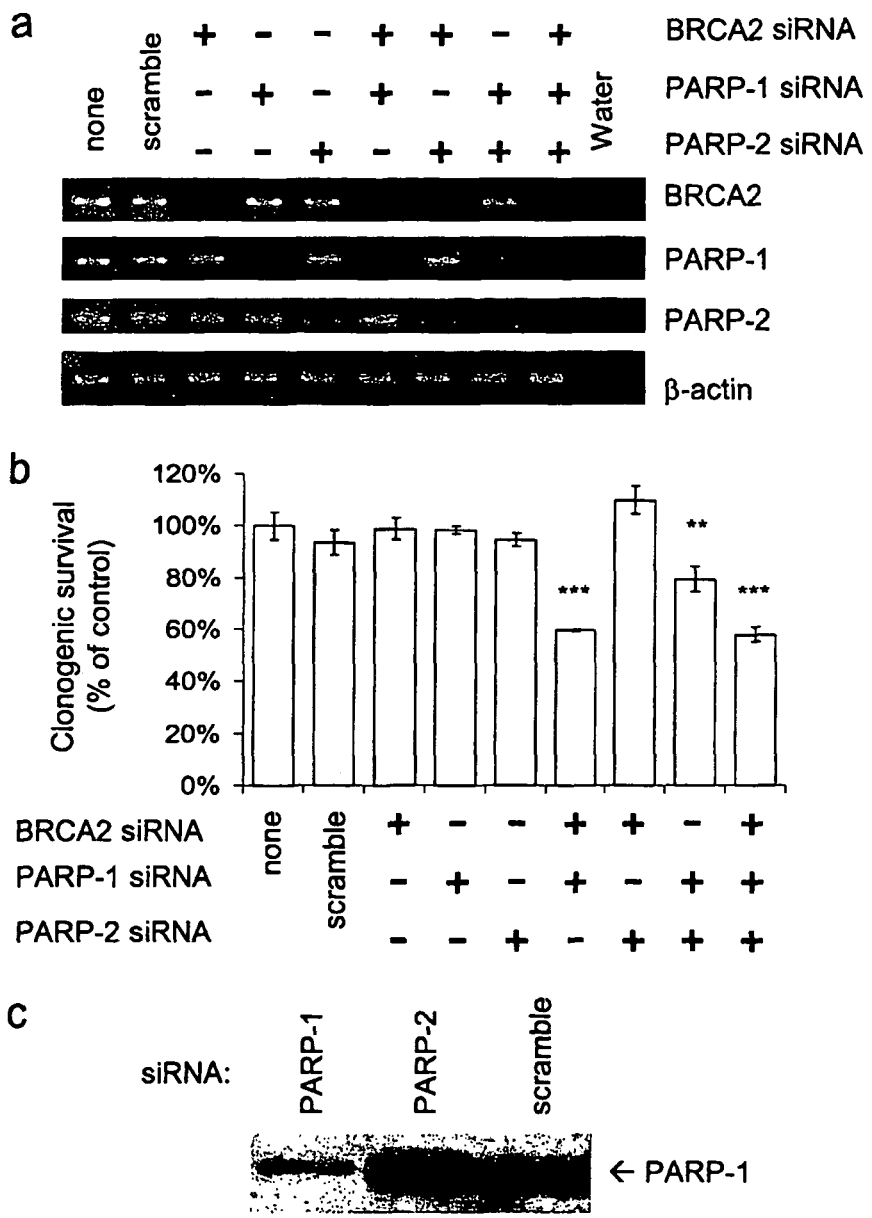

FIG. 6. PARP-1 and not PARP-2 is important in preventing formation of a recombinogenic lesion, causing death in absence of BRCA2. (a) RT-PCR on RNA isolated from SW480SN.3 cells treated with BRCA2, PARP-1 and PARP-2 siRNA in combinations as shown for 48 hours. (b) Clonogenic survival following 48-hours depletion of BRCA2, PARP-1 and PARP-2. The means (symbols) and standard deviation (bars) of at least three experiments are shown. Two and three stars designate statistical significance in t-test $p<0.01$ and $p<0.001$, respectively. (c) Western blot for PARP-1 in SW480SN.3 cells treated with different siRNA.

Figure 7:
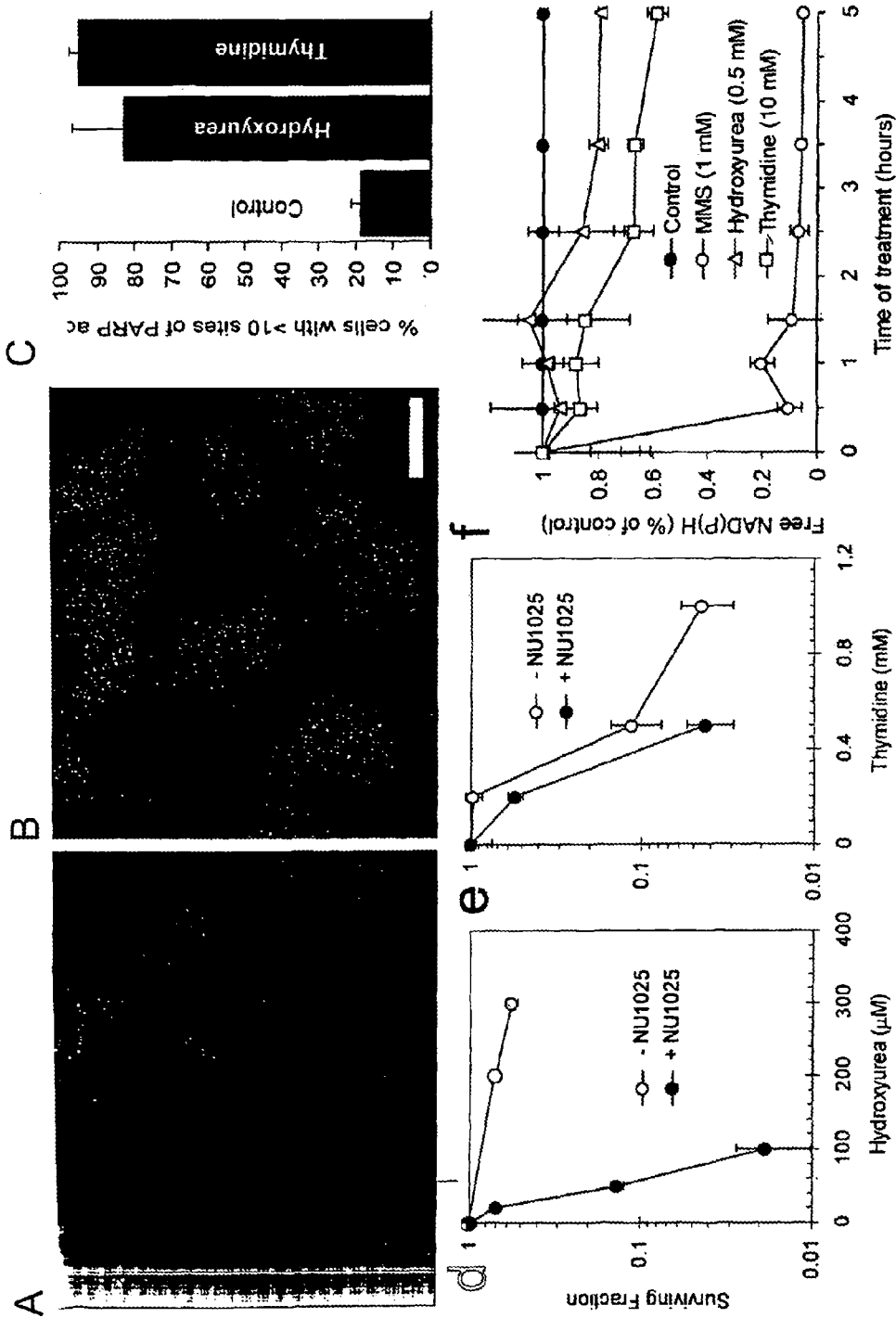

FIG. 7. (a) Visualisation of PAR polymers in untreated and (b) thymidine treated V79 cells (5 mM for 24 hours). (c) Percentage cells containing >10 sites of PARP activity following treatment with hydroxyurea (0.2 mM) and thymidine (5 mM). At least 300 nuclei were counted for each treatment and experiment. (d) Survival of V-C8+B2 cells following co-treatment with hydroxyurea or (e) thymidine and NU1025 (10 μM). (f) The activity of PARP was measured by the level of free NAD(P)H[11], following treatment with MMS, hydroxyurea (0.5 mM) or thymidine (10 mM). The means (symbol) and standard deviation (error bars) from at least three experiments are depicted.

Figure 8:
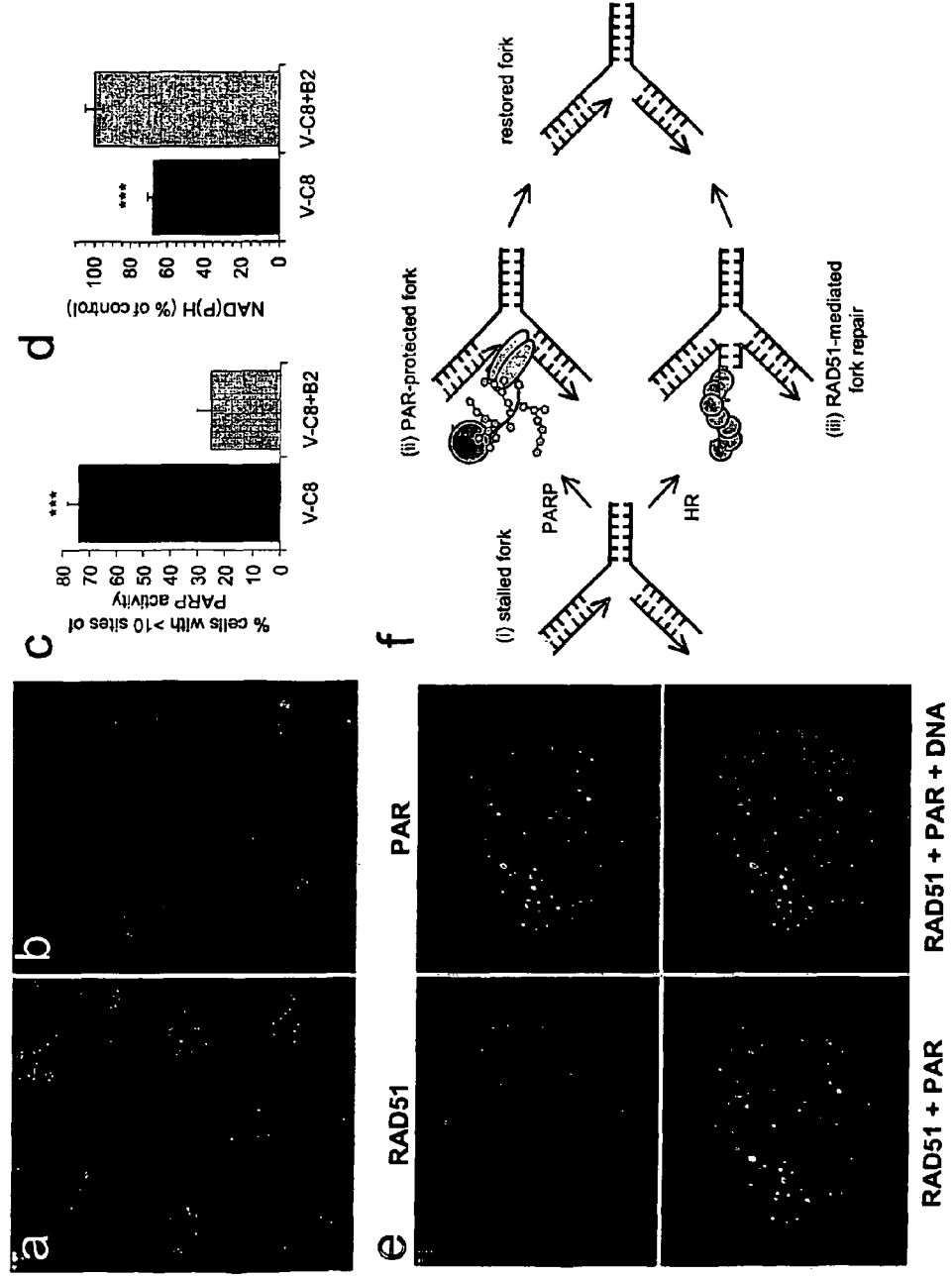

FIG. 8. (a) Visualisation of PAR polymers in untreated V-C8 and (b) V-C8+B2 cells. (c) Quantification of percentage cells containing >10 sites of PARP activity in untreated V-C8 and V-C8+B2 cells. (d) Level of NAD(P)H measured in untreated V-C8 and V-C8+B2 cells. Three stars designate $p<0.001$ in t-test. (e) Visualization of RAD51 and sites of PARP activity in V79 cells following a 24-hour thymidine treatment (5 mM). (f) A model for the role of PARP and HR at stalled replication forks.

FIG. 9 is the human cDNA sequence of PARP-1;
FIG. 10 is the human cDNA sequence of PARP-2;
FIG. 11 is the human cDNA sequence of PARP-3;
FIG. 12 is the human gDNA sequence of Tankyrase 1;
FIG. 13 is the human mRNA sequence of Tankyrase 2;
FIG. 14 is the human mRNA sequence of VPARP.

MATERIALS AND METHODS

Cytotoxicity of PARP Inhibitors to HR-Defective Cells: XRCC2, XRCC3 or BRCA2

Cell Culture

The irs1, irs1X2.1 and V79-4 cell lines were a donation from John Thacker [40] and the AA8, irs1SF and CXR3 cell lines were provided by Larry Thompson [41].

The VC-8, VC-8+B2, VC-8#13 were a gift from Malgorzata Zdzienicka [42]. All cell lines in this study were grown in Dulbecco's modified Eagle's Medium (DMEM) with 10% Foetal bovine serum and penicillin (100 U/ml) and streptomycin sulphate (100 μg/mL) at 37° C. under an atmosphere containing 5% $CO_2$.

Toxicity Assay—Colony Outgrowth Assay 500 cells suspended in medium were plated onto a Petri dish 4 hours prior to the addition of 3-AB, ISQ or NU1025. ISQ and NU1025 were dissolved in DMSO to a final concentration of 0.2% in treatment medium. 7-12 days later, when colonies could be observed, these colonies were fixed and stained with methylene blue in methanol (4 g/l). Colonies consisting of more than 50 cells were subsequently counted.

Apoptosis Experiments $0.25 \times 10^6$ cells were plated onto Petri dishes and grown for 4 hours before treatment with NU1025. After 72 hours, cells were trypsinized and resuspended with medium containing any floating cells from that sample. The cells were pelleted by centrifugation and resuspended for apoptosis analysis with FITC-conjugated annexin-V and propidium iodine (PI) (ApoTarget, Biosource International) according to manufacturer's protocol. Samples were analysed by flow cytometry (Becton-Dickenson FACSort, 488 nm laser), and percentage of apoptotic cells was determined by the fraction of live cells (PI-negative) bound with FITC-conjugated annexin-V.

Immunofluorescence

Cells were plated onto coverslips 4 h prior to 24-h treatments as indicated. Following treatments the medium was removed and coverslips rinsed once in PBS at 37° C. and fixed as described elsewhere [2]. The primary antibodies and dilutions used in this study were; rabbit polyclonal anti PAR (Trevigen; 1:500), goat polyclonal anti Rad51 (C-20, Santa Cruz; 1:200) and rabbit polyclonal anti Rad51 (H-92, Santa Cruz; 1:1000). The secondary antibodies were Cy-3-conjugated goat anti-rabbit IgG antibody (Zymed; 1:500), Alexa 555 goat anti-rabbit F(ab')$_2$IgG antibody (Molecular Probes; 1:500), Alexa 546 donkey anti-goat IgG antibody (Molecular Probes; 1:500) and Alexa 488 donkey anti-rabbit IgG antibody (Molecular Probes; 1:500). Antibodies were diluted in PBS containing 3% bovine serum albumin. DNA was stained with 1 μg/ml To Pro (Molecular Probes). Images were obtained with a Zeiss LSM 510 inverted confocal microscope using planapochromat 63X/NA 1.4 oil immersion objective and excitation wavelengths 488, 546 and 630 nm. Through focus maximum projection images were acquired from optical sections 0.50 μm apart and with a section thickness of 1.0 μm. Images were processed using Adobe PhotoShop (Abacus Inc). At least 300 nuclei were counted on each slide and those containing more than 10 RAD51 foci or sites of PARP activity were classified as positive.

PARP Activity Assays

A water-soluble tetrazolium salt (5 mM WST-8) was used to monitor the amount of NAD(P)H through its reduction to a yellow coloured formazan dye[43]. 5000 cells were plated in at least triplicate into wells of a 96 well plate and cultured in 100 μl normal growth media for 4 h at 37° C. CK8 buffer (Dojindo Molecular Technology, Gaithersburg, USA), containing WST-8, was then added either with or without treatment with DNA damaging agents at concentrations indicated. Reduction of WST-8 in the presence of NAD(P)H was determined by measuring visible absorbance ($OD_{450}$) every 30 min. A medium blank was also prepared containing just media and CK8 buffer. Changes in NAD(P)H levels were calculated by comparing the absorbance of wells containing cells treated with DNA damaging agents and those treated with DMSO alone. Alternately relative levels of NAD(P)H in different cells lines were calculated after 4 h incubation in CK8 buffer.

The ability of NU1025 to inhibit PARP-1 activity was also assayed in permeabilised cells using a modification of the method of Halldorsson et al [44], and described in detail elsewhere [45]. Briefly: 300 μl of NU1025-treated (15 min) permeabilised cells were incubated at 26° C. with oligonucleotide (final conc. 2.5 μg/ml), 75 μM NAD+[$^{32}$P] NAD (Amersham Pharmacia, Amersham, UK) in a total volume of 400 μl. The reaction was terminated after 5 min by adding ice cold 10% TCA 10% Na Ppi for 60 min prior to filtering through a Whatman GF/C filter (LabSales, Maidstone, UK), rinsed 6× with 1% TCA 1% NaPPi, left to dry and incorporated radioactivity was measured to determine PARP-1 activity. Data are expressed as pmol NAD incorporated/$10^6$ cells by reference to [$^{32}$P] NAD standards.

Pulse-Field Gel Electrophoresis $1.5 \times 10^6$ cells were plated onto 100 mm dishes and allowed 4 h for attachment. Exposure to drug was for 18 h after which cells were trypsinsied and $10^6$ cells melted into each 1% agarose insert. These inserts were incubated as described elsewhere (8) and separated by pulse-field gel electrophoresis for 24 h (BioRad; 120° angle, 60 to 240 s switch time, 4 V/cm). The gel was subsequently stained with ethidium bromide for analysis.

siRNA Treatment

Predesigned BRCA2 SMARTpool and scrambled siRNAs were purchased (Dharmacon, Lafayette, Colo.). 10000 cells seeded onto 6 well plates and left over night before transfected with 100 nM siRNA using Oligofectamine Reagent (Invitrogen) according to manufacturers instructions. Cells were then cultured in normal growth media for 48 h prior to trypsinisation and replating for toxicity assays. Suppression of BRCA2 was confirmed by Western blotting (as described previously [46]) of protein extracts treated with siRNA with an antibody against BRCA2 (Oncogene, Nottingham, UK).

EXAMPLES

Figure 1:
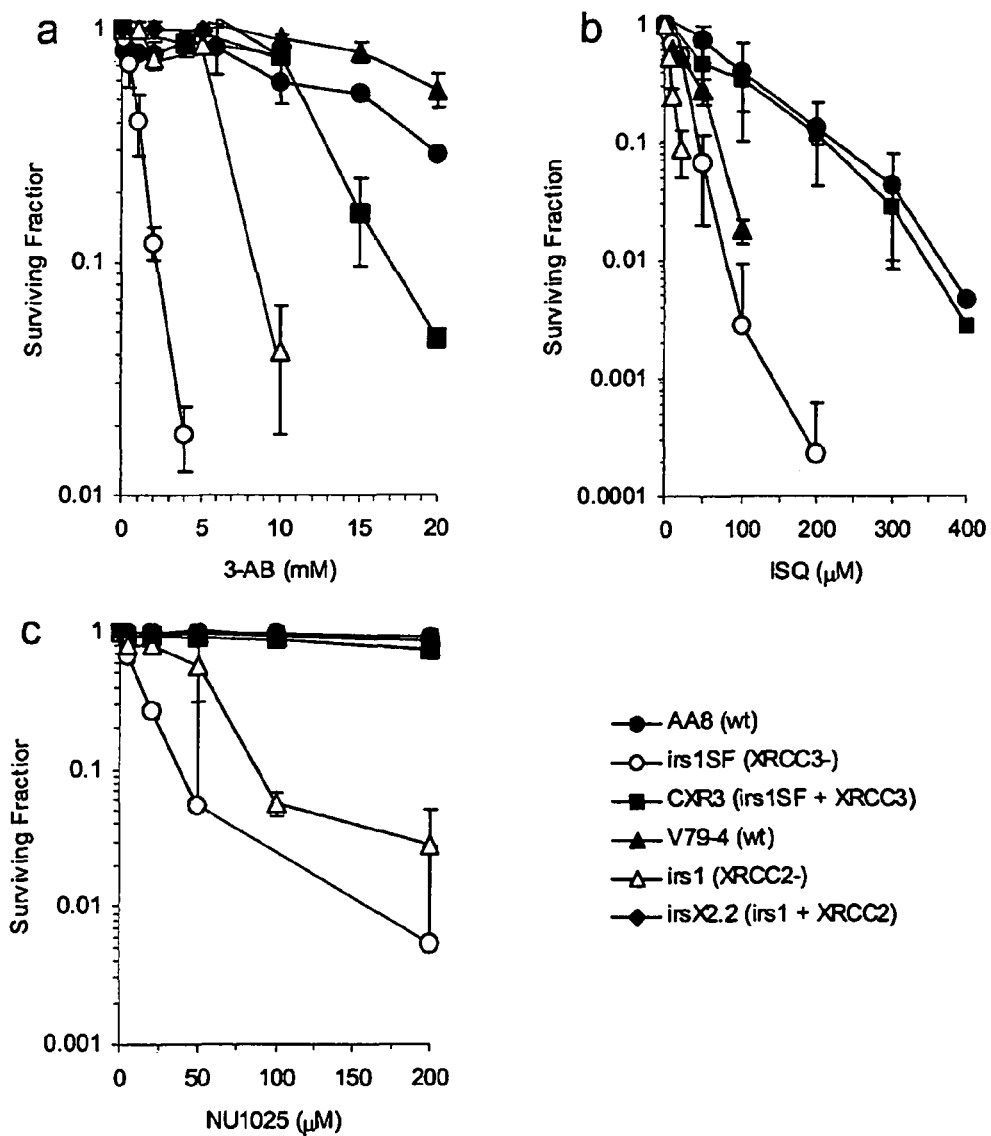

Homologous Recombination Deficient Cells are Hypersensitive to PARP-1 Inhibition To investigate the involvement of HR in cellular responses to inhibition of PARP-1, the effects of PARP-1 inhibitors on the survival of HR repair deficient cell lines were studied. It was found that cells deficient in HR (i.e., irs1SF which is defective in XRCC3 or irs1 which is defective in XRCC2 [see Table 1] were very sensitive to the toxic effect of 3-aminobenzamide (3-AB) and to two more potent inhibitors of PARP-1: 1,5-dihydroxyisoquinoline (ISQ; [37]) or 8-hydroxy-2-methylquinazolinone (NU1025 [38, 39]) (FIG. 1). The sensitivity in irs1SF cells to 3-AB, ISQ or NU1025 was corrected by the introduction of a cosmid containing a functional XRCC3 gene (CXR3). Similarly, the sensitivity in irs1 cells to 3-AB, ISQ or NU1025 was corrected by the introduction of a cosmid containing a functional XRCC2 gene (irs1X2.2).

BRCA2 Deficient Cells are Hypersensitive to PARP-1 Inhibition

Figure 2:
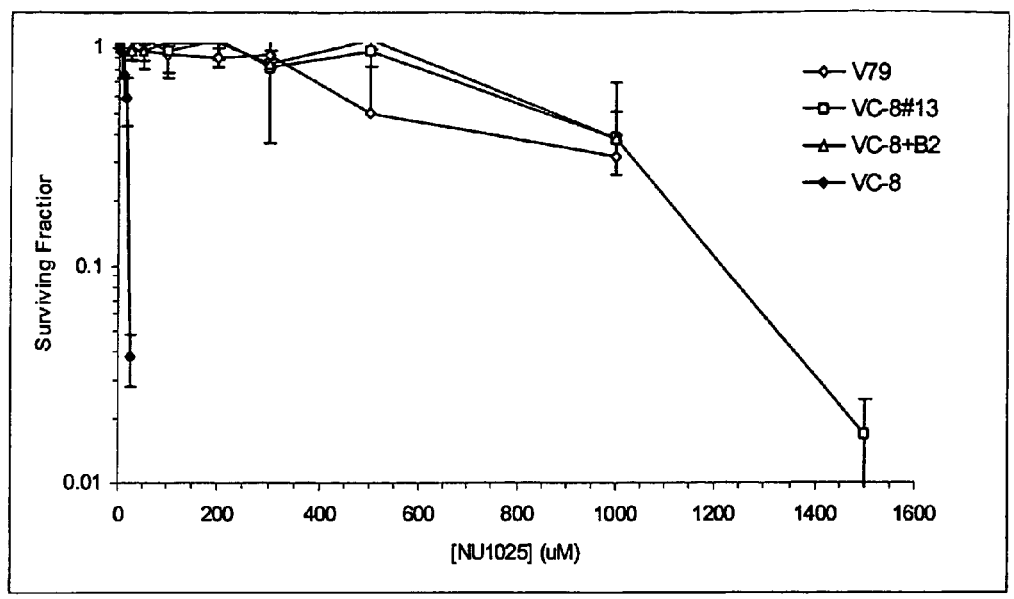
FIG. 2 is a graph showing cell survival in the presence of PARP inhibitor NU1025 in wt V79 cells, BRCA2 deficient VC-8 cells and VC-8 cells complimented with functional BRCA2 gene (VC-8#13, VC-8+B2). Colony outgrowth assay was used.

The survival of BRCA2 deficient cells (VC8) and wild type cells (V79Z) in the presence of inhibitors of PARP-1 was investigated. It was found that VC8 cells are very sensitive to the toxic effect of NU1025 (FIG. 2). The sensitivity in VC8 cells was corrected by the introduction of a functional BRCA2 gene either on chromosome 13 (VC8#13) or on an overexpression vector (VC8+B2). This result demonstrates that the sensitivity to PARP-1 inhibitors is a direct consequence of loss of the BRCA2 function.

Figure 3:
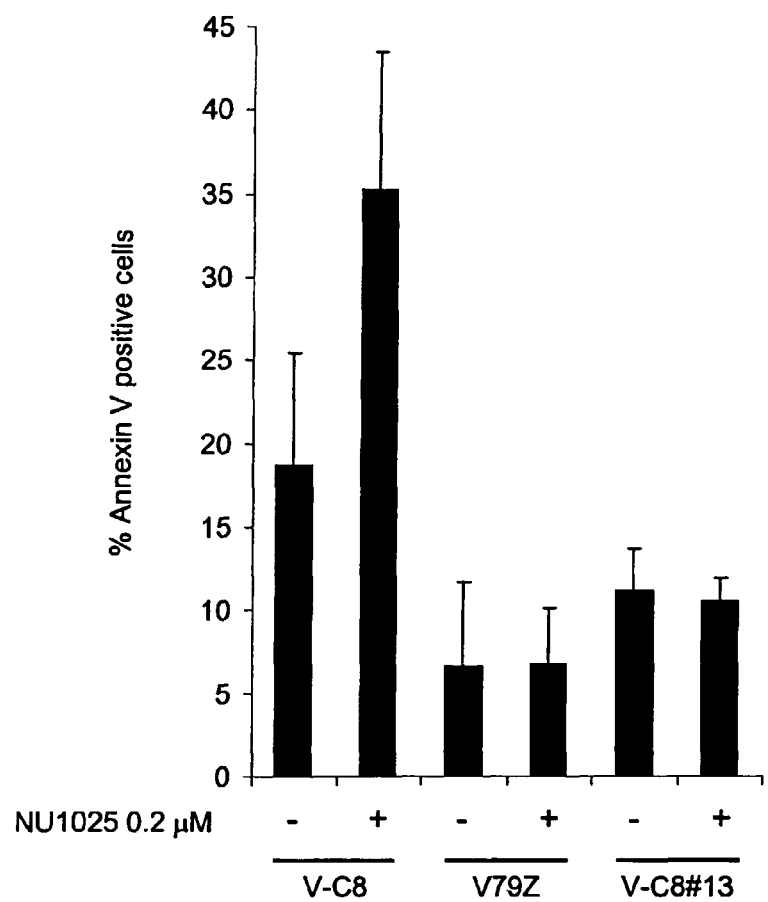
FIG. 3 is a histogram showing the percentage of the cells in apoptosis following a 72 hour incubation with NU1025.

To investigate if inhibition of PARP-1 triggers apoptosis in BRCA2 deficient cells, the level of apoptosis 72 hours following exposure to NU1025 was investigated. It was found that NU1025 triggered apoptosis only in VC8 cells, showing that loss of PARP-1 activity in BRCA2 deficient cells triggers this means of death (FIG. 3).

BRCA2 Deficient Breast Cancer Cells are Hypersensitive to PARP-1 Inhibition

It was examined whether the MCF7 (wild-type p53) and MDA-MB-231 (mutated p53) breast cancer cell lines displayed a similar sensitivity to NU1025 upon depletion of BRCA2. It was found that PARP inhibitors profoundly reduced the survival of MCF7 and MDA-MB-231 cells only when BRCA2 was depleted with a mixture of BRCA2 siRNA (FIG. 4). This shows that BRCA2 depleted breast cancer cells are sensitive to PARP inhibitors regardless of p53 status.

Figure 5A:
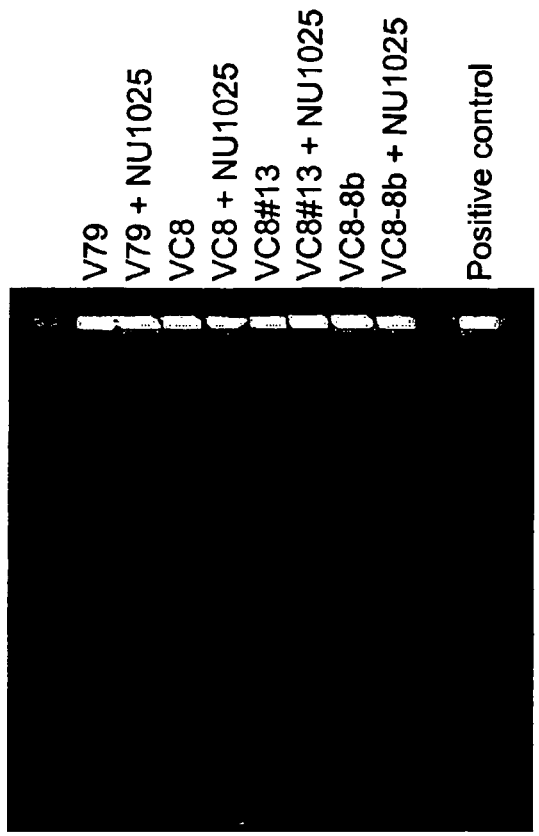

BRCA2 Deficient Cells Die from PARP-1 Inhibition in Absence of DNA Double-Strand Breaks (DSBs) but in Presence of γH2Ax HR is known to be involved in the repair of DSBs and other lesions that occur during DNA replication [2]. To determine whether the sensitivity of BRCA2 deficient cells is the result of an inability to repair DSBs following NU1025 treatment, the accumulation of DSBs in V79 and V-C8 cells was measured following treatments with highly toxic levels of NU1025. It was found that no DSBs were detectable by pulsed field gel electrophoretic analysis of DNA obtained from the treated cells (FIG. 5A), suggesting that low levels of DSBs or other recombinogenic substrates accumulated following PARP inhibition in HR deficient cells, which trigger γH2Ax FIG. 5B). The reason why BRCA2 deficient cells die following induction of these recombinogenic lesions is likely to be due to an inability to repair such lesions. To test this, the ability of BRCA2 deficient V-C8 cells and BRCA2 complimented cells to form RAD51 foci in response to NU1025 was determined. It was found that RAD51 foci were indeed induced in V-C8+B2 cells following treatment with NU1025 (statistically significant in t-test $p<0.05$; FIG. 5D). This indicates that the recombinogenic lesions trigger HR repair in these cells allowing them to survive. In contrast, the BRCA2 deficient V-C8 cells were unable to form RAD51 foci in response to NU1025 treatment (FIG. 5D) indicating no HR, which would leave the recombinogenic lesions unrepaired and thus cause cell death.

PARP-1 and Not PARP-2 is Important in Preventing Formation of a Recombinogenic Lesion There are two major PARPs present in the nucleus in mammalian cells, PARP-1 and PARP-2 and all reported PARP inhibitors inhibit both. In order to distinguish which PARP was responsible for the effect, we tested if the absence of PARP-1 and/or PARP-2 results in accumulation of toxic lesions, by depleting these and BRCA2 with siRNA in human cells (FIG. 6a). We found that the clonogenic survival was significantly reduced when both PARP-1 and BRCA2 proteins were co-depleted from human cells (FIG. 6b). Depletion of PARP-2 with BRCA2 had no effect on the clonogenic survival and depletion of PARP-2 in PARP-1 and BRCA2 depleted cells did not result in additional toxicity. These results suggest that PARP-1 and not PARP-2 is responsible for reducing toxic recombinogenic lesions in human cells. The cloning efficiency was only reduced to 60% of control in PARP-1 and BRCA2 co-depleted cells, while no HR deficient cells survived treatments with PARP inhibitors. This is likely to do with incomplete depletion of the abundant PARP-1 protein by siRNA (FIG. 6c), which might be sufficient to maintain PARP-1 function in some of the cells.

PARP-1 is Activated by Replication Inhibitors

HR is also involved in repair of lesions occurring at stalled replication forks, which may not involve detectable DSBs [2]. To test if PARP has a role at replication forks, PARP activation in cells treated cells with agents (thymidine or hydroxyurea) that retard or arrest the progression of DNA replication forks was examined. Thymidine depletes cells of dCTP and slows replication forks without causing DSBs. Hydroxyurea depletes several dNTP and block the replication fork, which is associated with the formation of DSBs at replication forks [2]. Both of these agents potently induce HR [2]. V79 hamster cells treated for 24 hours with thymidine or hydroxyurea were stained for PAR polymers. This revealed a substantial increase in the number of cells containing sites of PARP activity (FIG. 7C). This result suggests a function for PARP at stalled replication forks. It was also shown that inhibition of PARP with NU1025 enhances the sensitivity to thymidine or hydroxyurea in V-C8+B2 cells (FIG. 7D,E). This result suggests that PARP activity is important in repair of stalled replication forks or alternatively that it prevents the induction of death in cells with stalled replication forks.

PARP is rapidly activated at DNA single-strand breaks (SSB) and attracts DNA repair enzymes [3-6]. Methylmethane sulphonate (MMS) causes alkylation of DNA, which is repaired by base excision repair. PARP is rapidly activated by the SSB-intermediate formed during this repair, which depletes the NAD(P)H levels (FIG. 7F). We found that the activation of PARP and reduction of NAD(P)H levels is much slower following thymidine or hydroxyurea treatments. This slow PARP activation can be explained by the indirect action of thymidine and hydroxyurea and the time required to accumulate stalled replication forks as cells enter the S phase of the cell cycle.

PARP-1 and HR Have Separate Roles at Stalled Replication Forks

The number sites of PARP activity in untreated BRCA2 deficient V-C8 cells was determined. It was found that more V-C8 cells contain sites of PARP activity compared to V-C8+B2 cells (FIG. 8A,B,C). Also, the V-C8 cells have lower free NAD(P)H levels than the corrected cells (FIG. 8D), as a likely result of the increased PARP activity. Importantly these sites of PARP activity do not overlap with RAD51 foci (FIG. 8E).

The results herein suggest that PARP and HR have separate roles in the protection or rescue of stalled replication forks (FIG. 8F). A loss of PARP activity can be compensated by increased HR while a loss of HR can be compensated by increased PARP activity. However, loss of both these pathways leads to accumulation of stalled replication forks and to death, as in the case of PARP inhibited BRCA2 deficient cells.

As shown in the model outlined in FIG. 8F PARP and HR have complementary roles at stalled replication forks. (i) Replication forks may stall when encountering a roadblock on the DNA template. In addition, they may also stall temporarily, due to lack of dNTPs or other replication co-factors. (ii) PARP binds stalled replication forks or other replication-associated damage, triggering PAR polymerization. Resulting negatively charged PAR polymers may protect stalled replication forks, by repelling proteins that normally would process replication forks (e.g., resolvases), until the replication fork can be restored spontaneously when dNTPs or other co-factors become available. Alternatively, PAR polymers or PARP may attract proteins to resolve the replication block by other means. (iii) In absence of PARP activity, HR may be used as an alternative pathway to repair stalled replication forks. This compensatory model explains the increased level of HR and RAD51 foci found in PARP deficient cells[3-5] and higher PARP activity found in HR deficient cells (i.e. V-C8). Spontaneous replication blocks/lesions are only lethal in the absence of both PARP and HR.

TABLE 1

Genotype and origin of cell lines used in this study.

| Cell line | Genotype | Defect | Origin | Reference |
|---|---|---|---|---|
| AA8 | Wt | Wt | CHO | [41] |
| irs1SF | XRCC3⁻ | XRCC3⁻, deficient in HR | AA8 | [41] |
| CXR3 | XRCC3⁻ + hXRCC3 | Wt | irs1SF | [41] |
| V79-4 | Wt | Wt | V79 | [40] |
| irs1 | XRCC2⁻ | XRCC2⁻, deficient in HR | V79-4 | [40] |
| irs1X2.2 | XRCC2⁻ + hXRCC2 | Wt | irs1 | [40] |
| V79-Z | Wt | Wt | V79 | [42] |
| VC8 | BRCA2⁻ | BRCA2⁻, deficient in HR | V79-Z | [42] |
| VC8#13 | BRCA2⁻ + hBRCA2 | Wt | VC8 | [42] |
| VC8 + B2 | BRCA2⁻ + hBRCA2 | Wt | VC8 | [42] |

REFERENCES

[1] A. R. Venkitaraman Cancer susceptibility and the functions of BRCA1 and BRCA2, Cell 108 (2002) 171-182.
[2] C. Lundin, K. Erixon, C. Arnaudeau, N. Schultz, D. Jenssen, M. Meuth and T. Helleday Different roles for nonhomologous end joining and homologous recombination following replication arrest in mammalian cells, Mol Cell Biol 22 (2002) 5869-5878.
[3] D. D'Amours, S. Desnoyers, I. D'Silva and G. G. Poirier Poly(ADP-ribosyl)ation reactions in the regulation of nuclear functions, Biochem J 342 (1999) 249-268.
[4] Z. Herceg and Z. Q. Wang Functions of poly(ADP-ribose) polymerase (PARP) in DNA repair, genomic integrity and cell death, Mutat Res 477 (2001) 97-110.
[5] T. Lindahl, M. S. Satoh, G. G. Poirier and A. Klungland Post-translational modification of poly(ADP-ribose)polymerase induced by DNA strand breaks, Trends Biochem Sci 20 (1995) 405-411.
[6] M. S. Satoh and T. Lindahl Role of poly(ADP-ribose) formation in DNA repair, Nature 356 (1992) 356-358.

[7] S. Shall and G. de Murcia Poly(ADP-ribose)polymerase-1: what have we learned from the deficient mouse model?, Mutat Res 460 (2000) 1-15.

[8] Z. Q. Wang, L. Stingl, C. Morrison, M. Jantsch, M. Los, K Schulze-Osthoff and E. F. Wagner PARP is important for genomic stability but dispensable in apoptosis, Genes Dev 11 (1997) 2347-2358.

[9] C. M. Simbulan-Rosenthal, B. R. Haddad, D. S. Rosenthal, Z. Weaver, A. Coleman, R. Luo, H. M. Young, Z. Q. Wang, T. Ried and M. E. Smulson Chromosomal aberrations in PARP(−/−) mice: genome stabilization in immortalized cells by reintroduction of poly(ADP-ribose)polymerase cDNA, Proc Natl Acad Sci USA 96 (1999) 13191-13196.

[10] J. M. de Murcia, C. Niedergang, C. Trucco, M. Ricoul, B. Dutrillaux, M. Mark, F. J. Oliver, M. Masson, A. Dierich, M. LeMeur, C. Walztinger, P. Chambon and G. de Murcia Requirement of poly(ADP-ribose)polymerase in recovery from DNA damage in mice and in cells, Proc Natl Acad Sci USA 94 (1997) 7303-7307.

[11] F. d'Adda di Fagagna, M. P. Hande, W. M. Tong, P. M. Lansdorp, Z. Q. Wang and S. P. Jackson Functions of poly(ADP-ribose)polymerase in controlling telomere length and chromosomal stability, Nat Genet 23 (1999) 76-80.

[12] E. Samper, F. A. Goytisolo, J. Menissier-de Murcia, E. Gonzalez-Suarez, J. C. Cigudosa, G. de Murcia and M. A. Blasco Normal telomere length and chromosomal end capping in poly(ADP-ribose)polymerase-deficient mice and primary cells despite increased chromosomal instability, J Cell Biol 154 (2001) 49-60.

[13] C. Morrison, G. C. Smith, L. Stingl, S. P. Jackson, E. F. Wagner and Z. Q. Wang Genetic interaction between PARP and DNA-PK in V(D)J recombination and tumorigenesis, Nat Genet 17 (1997) 479-482.

[14] V. Schreiber, D. Hunting, C. Trucco, B. Gowans, D. Grunwald, G. De Murcia and J. M. De Murcia A dominant-negative mutant of human poly(ADP-ribose)polymerase affects cell recovery, apoptosis, and sister chromatid exchange following DNA damage, Proc Natl Acad Sci USA 92 (1995) 4753-4757.

[15] J. H. Kupper, M. Muller and A. Burkle Trans-dominant inhibition of poly(ADP-ribosyl)ation potentiates carcinogen induced gene amplification in SV40-transformed Chinese hamster cells, Cancer Res 56 (1996) 2715-2717.

[16] J. Magnusson and C. Ramel Inhibitor of poly(ADP-ribose)transferase potentiates the recombinogenic but not the mutagenic action of alkylating agents in somatic cells in vivo in Drosophila melanogaster, Mutagenesis 5 (1990) 511-514.

[17] A. S. Waldman and B. C. Waldman Stimulation of intra-chromosomal homologous recombination in mammalian cells by an inhibitor of poly(ADP-ribosylation), Nucleic Acids Res 19 (1991) 5943-5947.

[18] A. Semionov, D. Cournoyer and T. Y. Chow Inhibition of poly(ADP-ribose)polymerase stimulates extrachromosomal homologous recombination in mouse Ltk-fibroblasts, Nucleic Acids Res 27 (1999) 4526-4531.

[19] F. Dantzer, V. Schreiber, C. Niedergang, C. Trucco, E. Flatter, G. De La Rubia, J. Oliver, V. Rolli, J. Menissier-de Murcia and G. de Murcia Involvement of poly(ADP-ribose)polymerase in base excision repair, Biochimie 81 (1999) 69-75.

[20] F. Dantzer, G. de La Rubia, J. Menissier-De Murcia, Z. Hostomsky, G. de Murcia and V. Schreiber Base excision repair is impaired in mammalian cells lacking Poly(ADP-ribose)polymerase-1, Biochemistry 39 (2000) 7559-7569.

[21] L. Tentori, I. Portarena and G. Graziani Potential clinical applications of poly(ADP-ribose)polymerase (PARP) inhibitors, Pharmacol Res 45 (2002) 73-85.

[22] T. Lindahl and R. D. Wood Quality control by DNA repair, Science 286 (1999) 1897-1905.

[23] K. W. Caldecott DNA single-strand break repair and spinocerebellar ataxia, Cell 112 (2003) 7-10.

[24] D. D'Amours and S. P. Jackson The Mre11 complex: at the crossroads of dna repair and checkpoint signalling, Nat Rev Mol Cell Biol 3 (2002) 317-327.

[25] A. D. D'Andrea and M. Grompe The Fanconi anaemia/BRCA pathway, Nat Rev Cancer 3 (2003) 23-34.

[26] S. P. Jackson Sensing and repairing DNA double-strand breaks, Carcinogenesis 23 (2002) 687-696.

[27] R. Kanaar, J. H. Hoeijmakers and D. C. van Gent Molecular mechanisms of DNA double strand break repair, Trends Cell Biol 8 (1998) 483-489.

[28] D. C. van Gent, J. H. Hoeijmakers and R. Kanaar Chromosomal stability and the DNA double-stranded break connection, Nat Rev Genet 2 (2001) 196-206.

[29] S. L. Neuhausen and E. A. Ostrander Mutation testing of early-onset breast cancer genes BRCA1 and BRCA2, Genet Test 1 (1997) 75-83.

[30] G. Kuperstein, W. D. Foulkes, P. Ghadirian, J. Hakimi and S. A. Narod A rapid fluorescent multiplexed-PCR analysis (FMPA) for founder mutations in the BRCA1 and BRCA2 genes, Clin Genet 57 (2000) 213-220.

[31] A. Chiarugi Poly(ADP-ribose)polymerase: killer or conspirator? The 'suicide hypothesis' revisited, Trends Pharmacol Sci 23 (2002) 122-129.

[32] C. R. Calabrese, M. A. Batey, H. D. Thomas, B. W. Durkacz, L. Z. Wang, S. Kyle, D. Skalitzky, J. Li, C. Zhang, T. Boritzki, K. Maegley, A. H. Calvert, Z. Hostomsky, D. R. Newell and N. J. Curtin Identification of Potent Nontoxic Poly(ADP-Ribose)Polymerase-1 inhibitors: Chemopotentiation and Pharmacological Studies, Clin Cancer Res 9 (2003) 2711-2718.

[33] D. Ferraris, Y. S. Ko, T. Pahutski, R. P. Ficco, L. Serdyuk, C. Alemu, C. Bradford, T. Chiou, R. Hoover, S. Huang, S. Lautar, S. Liang, Q. Lin, M. X. Lu, M. Mooney, L. Morgan, Y. Qian, S. Tran, L. P. Williams, Q. Y. Wu, J. Zhang, Y. Zou and V. Kalish Design and synthesis of poly ADP-ribose polymerase-1 inhibitors. 2. Biological evaluation of aza-5[H]-phenanthridin-6-ones as potent, aqueous-soluble compounds for the treatment of ischemic injuries, J Med Chem 46 (2003) 3138-3151.

[34] K. J. Dillon, G. C. Smith and N. M. Martin A FlashPlate assay for the identification of PARP-1 inhibitors, J Biomol Screen 8 (2003) 347-352.

[35] A. J. Pierce, R. D. Johnson, L. H. Thompson and M. Jasin XRCC3 promotes homology-directed repair of DNA damage in mammalian cells, Genes Dev 13 (1999) 2633-2638.

[36] R. D. Johnson, N. Liu and M. Jasin Mammalian XRCC2 promotes the repair of DNA double-strand breaks by homologous recombination, Nature 401 (1999) 397-399.

[37] G. M. Shah, D. Poirier, S. Desnoyers, S. Saint-Martin, J. C. Hoflack, P. Rong, M. ApSimon, J. B. Kirkland and G. G. Poirier Complete inhibition of poly(ADP-ribose)polymerase activity prevents the recovery of C3H10T1/2 cells from oxidative stress, Biochim Biophys Acta 1312 (1996) 1-7.

[38] R. J. Griffin, S. Srinivasan, K. Bowman, A. H. Calvert, N. J. Curtin, D. R. Newell, L. C. Pemberton and B. T. Golding Resistance-modifying agents. 5. Synthesis and biological properties of quinazolinone inhibitors of the DNA repair enzyme poly(ADP-ribose)polymerase (PARP), J Med Chem 41 (1998) 5247-5256.

[39] S. Boulton, L. C. Pemberton, J. K. Porteous, N. J. Curtin, R. J. Griffin, B. T. Golding and B. W. Durkacz Potentiation of temozolomide-induced cytotoxicity: a comparative study of the biological effects of poly(ADP-ribose)polymerase inhibitors, Br J Cancer 72 (1995) 849-856.

[40] C. S. Griffin, P. J. Simpson, C. R. Wilson and J. Thacker Mammalian recombination-repair genes XRCC2 and XRCC3 promote correct chromosome segregation, Nat Cell Biol 2 (2000) 757-761.

[41] R. S. Tebbs, Y. Zhao, J. D. Tucker, J. B. Scheerer, M. J. Siciliano, M. Hwang, N. Liu, R. J. Legerski and L. H. Thompson Correction of chromosomal instability and sensitivity to diverse mutagens by a cloned cDNA of the XRCC3 DNA repair gene, Proc Natl Acad Sci USA 92 (1995) 6354-6358.

[42] M. Kraakman-van der Zwet, W. J. Overkamp, R. E. van Lange, J. Essers, A. van Duijn-Goedhart, I. Wiggers, S. Swaminathan, P. P. van Buul, A. Errami, R. T. Tan, N. G. Jaspers, S. K. Sharan, R. Kanaar and M. Z. Zdzienicka Brca2 (XRCC11) deficiency results in radioresistant DNA synthesis and a higher frequency of spontaneous deletions, Mol Cell Biol 22 (2002) 669-679.

[43] J. Nakamura, S. Asakura, S. D. Hester, G. de Murcia, K. W. Caldecott and J. A. Swenberg Quantitation of intracellular NAD(P)H can monitor an imbalance of DNA single strand break repair in base excision repair deficient cells in real time, Nucleic Acids Res 31 (2003) e104.

[44] H. Halldorsson, D. A. Gray and S. Shall Poly(ADP-ribose)polymerase activity in nucleotide permeable cells, FEBS Lett 85 (1978) 349-352.

[45] K. Grube, J. H. Kupper and A. Burkle Direct stimulation of poly(ADP ribose)polymerase in permeabilized cells by double-stranded DNA oligomers, Anal Biochem 193 (1991) 236-239.

[46] C. Lundin, N. Schultz, C. Amaudeau, A. Mohindra, L. T. Hansen and T. Helleday RAD51 is Involved in Repair of Damage Associated with DNA Replication in Mammalian Cells, J Mol Biol 328 (2003) 521-535.

[47] Schreider et al., Journal of Biological Chemistry 277: 23028-23036 (2002).

---

The invention claimed is:

1. A method of treatment of cancer cells defective in homologous recombination (HR), the method comprising:
 identifying a human patient with a familial predisposition to gene-linked hereditary cancer, wherein said cancer comprises cancer cells defective in homologous recombination;
 identifying a compound which inhibits PARP-1, and administering to said human patient a therapeutically effective amount of said compound.

* * * * *